(12) United States Patent
ElSohly et al.

(10) Patent No.: US 10,099,995 B2
(45) Date of Patent: Oct. 16, 2018

(54) RESVERATROL ESTERS

(71) Applicants:Mahmoud A. ElSohly, Oxford, MS (US); Waseem Gul, Oxford, MS (US); Jeptha N. Cole, Jackson, MS (US)

(72) Inventors: Mahmoud A. ElSohly, Oxford, MS (US); Waseem Gul, Oxford, MS (US); Jeptha N. Cole, Jackson, MS (US)

(73) Assignee: Cole Research and Design, LLC, Jackson, MS (US)

( * ) Notice: Subject to any disclaimer, the term of this patent is extended or adjusted under 35 U.S.C. 154(b) by 0 days.

(21) Appl. No.: 15/389,674

(22) Filed: Dec. 23, 2016

(65) Prior Publication Data

US 2017/0183290 A1 Jun. 29, 2017

Related U.S. Application Data

(60) Provisional application No. 62/387,588, filed on Dec. 24, 2015.

(51) Int. Cl.
*C07C 69/42* (2006.01)
*C07C 67/08* (2006.01)

(52) U.S. Cl.
CPC .............. *C07C 69/42* (2013.01); *C07C 67/08* (2013.01)

(58) Field of Classification Search
None
See application file for complete search history.

(56) References Cited

U.S. PATENT DOCUMENTS

| 7,026,518 | B2* | 4/2006 | Gokaraju | A61K 8/347 568/729 |
|---|---|---|---|---|
| 2001/0041684 | A1 | 11/2001 | Lezdey et al. | |
| 2008/0057088 | A1 | 3/2008 | Blass et al. | |
| 2008/0139507 | A1 | 6/2008 | Gupta | |
| 2009/0220450 | A1 | 9/2009 | Green et al. | |
| 2011/0038965 | A1 | 2/2011 | McKay et al. | |
| 2011/0245345 | A1 | 10/2011 | Amato et al. | |
| 2013/0108700 | A1 | 5/2013 | Nguyen | |
| 2013/0267547 | A1* | 10/2013 | Gerk | A61K 31/426 514/274 |
| 2014/0275266 | A1 | 9/2014 | Wang et al. | |
| 2015/0005391 | A1 | 1/2015 | Cole | |
| 2017/0281563 | A1 | 10/2017 | Cole | |

FOREIGN PATENT DOCUMENTS

| CN | 102675100 | 9/2012 |
|---|---|---|
| CN | 103508981 | 1/2014 |
| EP | 2 522 330 | 11/2012 |
| WO | 2004/000302 | 12/2003 |
| WO | 2007/143631 | 12/2007 |
| WO | 2012/048204 | 4/2012 |
| WO | 2012/129499 | 9/2012 |
| WO | 2013/068758 | 5/2013 |
| WO | 2014/126370 | 8/2014 |
| WO | PCT/US2014/044338 | 10/2014 |
| WO | 2014/210308 | 12/2014 |
| WO | PCT/US2014/044338 | 1/2016 |
| WO | PCT/US2015/054758 | 3/2016 |
| WO | 2016/057831 | 4/2016 |

(Continued)

OTHER PUBLICATIONS

CAPLUS printout of Foreign Patent No. CN103508981. (Year: 2014).*

(Continued)

*Primary Examiner* — Po-Chih Chen
(74) *Attorney, Agent, or Firm* — Evan Law Group LLC

(57) ABSTRACT

A resveratrol ester has the following structure:

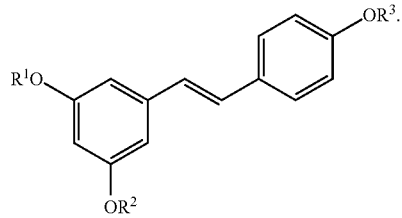

$R^1$, $R^2$ and $R^3$ are H or

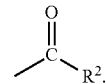

Each $R^4$ is independently a carbon chain of 2 to 4 carbon atoms comprising a terminal carboxylic acid moiety, a carbon chain of 1 to 5 carbon atoms comprising an amine moiety, or

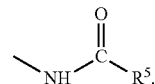

$R^5$ is a carbon chain of 3 or 4 carbon atoms having a terminal carboxylic acid moiety. At least one of $R^1$, $R^2$ and $R^3$ is

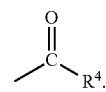

Salts of resveratrol esters are also included.

19 Claims, 14 Drawing Sheets

(56) References Cited

FOREIGN PATENT DOCUMENTS

| WO | 2017/019709 | 2/2017 |
|---|---|---|
| WO | PCT/US2017/020980 | 11/2017 |

OTHER PUBLICATIONS

CAPLUS printout of Foreign Patent No. CN102675100. (Year: 2012).*
Ehrlich, H. et al., "Regulation of wound healing from a connective tissue perspective", Wound Repair and Regeneration, vol. 4, issue 2, pp. 203-210, (1996).
Leung, A. et al., "Fetal wound healing: implictions for minimal scar formation", Current Opinion in Pediatrics, vol. 24, No. 3, pp. 371-378, (2012).
Manuel, J. et al., "Matrix metalloproteinase 9 (MMP-9) is upregulated during scarless wound healing in athymic nude mice", Matrix Biology, vol. 25, pp. 505-514, (2006).
Seifert, A.W. et al., "Skin regeneration in adult axolotls: a blueprint for scar-free healing in vertebrates", PLoS One, vol. 7, issue 4, pp. 1-19, (2012).
Polette, M. et al., "Tumor invasion and matrix metalloproteinases", Critical Reviews in Oncology Hematology, vol. 49, pp. 179-186, (2004).
Salo, T. et al., "Expression of matrix metalloproteinase-2 and -9 during early human wound healing", Laboratory Investigation, vol. 70, No. 2, pp. 176-182, (1994).
Giannelis, G., "Matrix metalloproteinases in scarless wound healing", Electronic Theses and Dissertations, pp. 1-119, (2011), available at hdl.handle.net/2429/36241.
Guo, M-S. et al., "Hyaluronic acid increases MMP-2 and MMP-9 expressions in cultured trabecular meshwork cells from patients with primary open-angle glaucoma", Molecular Vision, vol. 18, pp. 1175-1181, (2012).
Ndiaye, M. et al., "The grape antioxidant resveratrol for skin disorders: promise, prospects, and challenges", Arch Biochem Biophys., vol. 508, No. 2, pp. 164-170, (2011).
Gweon, E.J. et al., "Resveratrol induces MMP-9 and cell migration via the p38 kinase and PI-3K pathways in HT1080 human fibrosarcoma cells", Oncology Reports, vol. 29, No. 2, pp. 826-834, (2013).
Ghosh, S. et al., "Resveratrol activates SIRT1 in a Lamin A-dependent manner", Cell Cycle, vol. 12, No. 6, pp. 872-876, (2013).
Blander, G. et al., "SIRT1 promotes differentiation of normal human keratinocytes", Journal of Investigative Dermatology, vol. 129, No. 1, pp. 41-49, (2009).
Thompson, N.L. et al., "Expressions of transforming growth factor-β1 in specific cells and tissues of adult and neonatal mice", The Journal of Cell Biology, vol. 108, pp. 661.669, (1989).
Midgley, A. et al., "Transforming growth factor-β1 (TGF-β1)-stimulated fibroblast to myofibroblast differentiation is mediated by hyaluronan (HA)-facilitated epidermal growth factor receptor (EGFR) and CD44 co-localization in lipid rafts", Journal of Biological Chemistry, vol. 288, No. 21, pp. 14824-14838, (2013).
Busch, F. et al., "Sirt-1 is required for the inhibition of apoptosis and inflammatory responses in human tenocytes", Journal of Biological Chemistry, vol. 287, No. 31, pp. 25770-25781, (2012).
Spallotta, F. et al., "A nitric oxide-dependent cross-talk between class I and III histone deacetylases accelerates skin repair", Journal of Biological Chemistry, vol. 288, No. 16, pp. 11004-11012, (2013).
Pastore, S. et al., "Resveratrol induces long-lasting IL-8 expression and peculiar EGFR activation/distribution in human keratinocytes: Mechanisms and implications for skin administration", PLOS One, vol. 8, issue 3, pp. 1-14, (2013).
Jiang, W.G. et al., "Influence of interleukin-8 (IL-8) and IL-8 receptors on the migration of human keratinocytes, the role of PLC-gamma and potential clinical implications", Experimental and Therapeutic Medicine, vol. 3, No. 2, pp. 231-236, (2012).
Steiger, S. et al., "Neutrophil cannibalism triggers transforming growth factor β1 production and self regulation of neutrophil inflammatory function in monosodium urate monohydrate crystal-induced inflammation in mice", Arthritis & Rheumatism, vol. 65, No. 3, pp. 815-823, (2013).
Holian, O. et al., "Resveratrol inhibits the proliferation of normal human keratinocytes in vitro", Journal of Cellular Biochemistry Supplement, supplement 36, pp. 55-62, (2001).
Kim, J-J. et al., "The role of SIRT1 on angiogenic and odontogenic potential in human dental pulp cells", Journal of endodontics, vol. 38, No. 7, pp. 899-906, (2012).
Williams, L.D. et al., "Safety studies conducted on high-purity trans-resveratrol in experimental animals", Food and Chemical Toxicology, vol. 47, No. 9, pp. 2170-2182, (2009).
Polonini, H.C. et al., "Photoprotective activity of resveratrol analogues", Bioorganic & Medicinal Chemistry, vol. 21, No. 4, pp. 964-968, (2013).
Hung, C-F. et al., "Delivery of resveratrol, a red wine polyphenol, from solutions and hydrogels via the skin", Biological & Pharmaceutical Bulletin, vol. 31, No. 5, pp. 955-962, (2008).
Alonso, C. et al, "Antioxidant cosmeto-textiles: skin assessment", European Journal of Pharmaceutics and Biopharmaceutics, vol. 84, No. 1, pp. 192-199, (2013).
Fagone, E. et al., "Resveratrol inhibits transforming growth factor-β-induced proliferation and differentiation of ex vivo human lung fibroblasts into myofibroblasts through ERK/Akt inhibition and PTEN restoration", Experimental Lung Research, vol. 37, No. 3, pp. 162-174, (2011).
Sheu, S-Y. et al., "Biological characterization of oxidized hyaluronic acid/resveratrol hydrogel for cartilage tissue engineering", Journal of Biomedical Materials Research Part A, vol. 101, issue 12, pp. 3457-3466, (2013).
Fearmonti, R. et al., "A review of scar scales and scar measuring devices", Eplasty, vol. 10, pp. 354-363, (2010).
Nayor, D. et al., "Living longer, healthier lives with resveratrol", Le Magazine, 12 pages, found at www.lef.org, (2008).
Definition of "Resveratrol", Wikipedia, the free encyclopedia, found at www.en.wikipedia.org/wiki/Resveratrol, pp. 1-14, printed on Jun. 21, 2013.
NEW-SKIN® Liquid Bandage, Cover. Protect. Prevent., www.newskinproducts.com/liquid-bandages/liquid-bandage/, pp. 1-10, printed on Apr. 26, 2015.
Edward, M. et al., "Keratinocytes stimulate fibroblast hyaluronan synthesis through the release of stratifin: A possible role in the suppression of scar tissue formation", Wound Repair and Regeneration, vol. 19, pp. 379-386, (2011).
International Search Report dated Oct. 9, 2014 for PCT Application No. PCT/US2014/044338, 13 pages.
Lorena D. et al., "Normal scarring: importance of myofibroblasts", Wound Repair and Regeneration, vol. 10, No. 2, pp. 86-92, (2002).
Yaman, I. et al., "Effects of resveratrol on incisional wound healing in rats", Surgery Today, vol. 43, No. 12, pp. 1433-1438, (2013).
Fehrholz, M. et al., "Caffeine and rolipram affect smad signaling and TGF-β1 stimulated CTGF and transgelin expression in lung epithelial cells", PLOS One, vol. 9, issue 5, pp. 1-11, (2014).
Gressner, O.A. et al., "Identification of paraxanthine as the most potent caffeine-derived inhibitor of connective tissue growth factor expression in liver parenchymal cells", Liver International, vol. 29, No. 6, pp. 886-897, (2009).
Herman, A. et al., "Caffeine's mechanisms of action and its cosmetic use", Skin Pharmacology and Physiology, vol. 26, No. 1, pp. 8-14, (2013).
Inder, M.K. et al., "Bovine popular stomatitis virus encodes a functionally distinct BEGF that binds both VEGFR-1 and VEGFR-2", Journal of General Virology, vol. 88, pp. 781-791, (2007).
Lee, S. et al., "Effect of a broad-specificity chemokine-binding protein on brain leukocyte infiltration and infarct development", Stroke, vol. 46, pp. 537-544, (2015).
Ojeh, N. et al., "The effects of caffeine on wound healing", International Wound Journal, pp. 1-9, (2014).
Jagtap, S. et al., "All-trans retinoic acid and basic fibroblast growth factor synergistically direct pluripotent human embryonic stem cells to extraembryonic lineages", Stem Cell Research, vol. 10, pp. 228-240, (2013).

(56) References Cited

OTHER PUBLICATIONS

Cao, K. et al., "Progerin and telomere dysfunction collaborate to trigger cellular senescence in normal human fibroblasts", The Journal of Clinical Investigation, vol. 121, No. 7, pp. 2833-2844, (2011).
Machesney, M. et al., "Activated keratinocytes in the epidermis of hypertrophic scars", American Journal of Pathology, vol. 152, No. 5, pp. 1133-1141, (1998).
Demidenko, Z.N. et al., "At concentrations that inhibit mTOR, resveratrol suppresses cellular senescence", Cell Cycle, vol. 8, No. 12, pp. 1901-1904, (2009).
Bennett, R.D. et al., "Calmodulin-like protein upregulates myosin-10 in human keratinocytes and is regulated during epidermal wound healing in vivo", Journal of Investigative Dermatology, vol. 129, pp. 765-769, (2009).
Lansdown, A.B.G. et al., "Zinc in wound healing: Theoretical, experimental, and clinical aspects", Wound Repair and Regeneration, vol. 15, pp. 2-16, (20071.
Bennett, R.D. et al., "Calmodulin-like protein increases filopodia-dependent cell motility via up-regulation of myosin-10*", The Journal of Biological Chemistry, vol. 282, No. 5, pp. 3205-3212, (2007).
Skelding, K.A. et al., "Controlling the cell cycle: The role of calcium/calmodulin-stimulated protein kinases I and II", Cell Cycle, vol. 10, issue 4, pp. 631-639, (2011).
Chifflet, S. et al., "Early and late calcium waves during wound healing in corneal endothelial cells", Wound Repair and Regeneration, vol. 20, pp. 28-37, (2012).
Lansdown, A.B.G., "Calcium: a potential central regulator in wound healing in the skin", Wound Repair and Regeneration, vol. 10, No. 5, pp. 271-285, (2002).
Grzesiak, J.J. et al., "Changes in the concentrations of extracellular $Mg^{++}$ and $Ca^{++}$ down-regulate e-cadherin and up-regulate $\alpha_2\beta_1$ integrin function, activating keratinocyte migration on type I collagen", Journal of Investigative Dermatology, vol. 104, pp. 768-774, (1995).
Ferreira, A.M. et al., "Diminished induction of skin fibrosis in mice with MCP-1 deficiency" Journal of Investigative Dermatology, vol. 126, pp. 1900-1908, (2006).
Ishimoto, T. et al., "Downregulation of monocyte chemoattractant protein-1 involving short interfering RNA attenuates hapten-induced contact hypersenistivity", Molecular Therapy, vol. 16, No. 2, pp. 387-395, (2008).
De Filippo, K. et al., "Mast cell and macrophage chemokines CXCL1/CXCL2 control the early stage of neutrophil recruitment during tissue inflammation", Blood, vol. 121, No. 24, pp. 4930-4937, (2013).

Qu, L. et al., "Disruption of TLR3 signaling due to cleavage of TRIF by the Hepatitis A virus protease-polymerase processing intermediate, 3CD", PLoS Pathogens, vol. 7, issue 9, pp. 1-13, (2011).
Xiang, Z. et al., "Enterovirus 68 3C protease cleaves TRIF to attenuate antiviral responses mediated by toll-like receptor 3", Journal of Virology, vol. 68, No. 12, pp. 6650-6659, (2014).
Farina, G. et al., "sdRNA activation of endothelin-1 and markers of vascular activation in endothelial cells and fibroblasts", Ann Rheum Dis, vol. 70, pp. 544-550, (2011).
Kim, M.Y. et al., "Hyaluronic acid oligosaccharides suppress TLR3-dependent cytokine expression in a TLR4-dependent manner", PLoS One, vol. 8, issue 8, pp. 1-7, (2013).
Product description of "CCL2 (ID 6347) Trilencer-27 Human siRNA", amsbio, AMS Biotechnology, 1 page, found at www.amsbio.com/datasheets/SR304273.pdf, printed on Sep. 9, 2014.
Product description of "MCP-1 siRNA (h): sc-43913", Santa Cruz Biotechnology, Inc., 1 page, found at www.scbt.com/datasheet-43913-mcp-1-sirna-h.html, printed on Sep. 9, 2014.
Press Release "Turning spiegelmers into drugs", Noxxon Pharma Ag, 2 pages, found at www.noxxon.com/downloads/FactSheet.pdf, (2014).
Seet, B.T. et al., "Viral chemokine-binding proteins", Journal of Leukocyte Biology, vol. 72, pp. 24-34, (2002).
International Search Report dated Mar. 3, 2016 for PCT Application No. PCT/US2015/054758, 20 pages.
Choi, H-R. et al., "Oligosaccharides of hyaluronic acid increased epidermal cell stemness by modulation of integrin expression", Journal of Cosmetic Dermatology, vol. 11, No. 4, pp. 290-296, (2012).
Pascual-Marti, M.C. et al., "Supercritical fluid extraction of resveratrol from grape skin of vitis vinifera and determination by HPLC", Talanta vol. 54, pp. 735-740, (2001).
Khanna, S. et al., "Dermal wound healing properties of redox-active grape seed proanthocyanidins", Free Radical Biology & Medicine, vol. 33, No. 8, pp. 1089-1096, (2002).
International Search Report dated Nov. 7, 2017 for PCT Application No. PCT/US2017/020980.
7 pages, Sep. 4, 2015, U.S. Appl. No. 14/313,338.
17 pages, May 9, 2016, U.S. Appl. No. 14/313,338.
5 pages, Jan. 5, 2018, U.S. Appl. No. 15/492,766.
U.S. Appl. No. 15/492,766, filed Apr. 20, 2017.
Zhu et al., "Effect of resveratrol on human scar fibroblasts and scar-derived fibroblasts of rabbit ears", Chinese Journal of Natural Medicine, vol. 8, No. 1, pp. 7-9, (2006). (Eng. abstract only).
Translation of Zhu et al., "Effect of resveratrol on human scar fibroblasts and scar-derived fibroblasts of rabbit ears", Chinese Journal of Natural Medicine, vol. 8, No. 1, pp. 7-9, (2006), prepared Nov. 2016.
Mailed Jan. 25, 2018, Application No. 14742647.2, EP.
Mailed May 14, 2018, U.S. Appl. No. 15/492,776.

* cited by examiner

FIG. 14

RESVERATROL ESTERS

BACKGROUND

Resveratrol (trans-3,4',5-trihydroxystilbene), a stilbenoid, is a natural polyphenol present in various plants, some food products, red wine and grapes. Resveratrol has the following chemical structure:

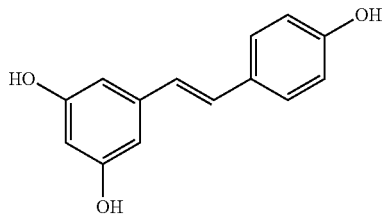

Resveratrol possesses anti-inflammatory, anti-carcinogenic and anti-oxidant properties, and has been extensively studied. Huge interest in resveratrol was created when it was discovered that it was able to activate the SIRT1 gene, a gene implicated in the life span extension associated with calorie-restricted diets. However, beneficial effects have been challenging to observe in human clinical studies.

It was recently discovered that application of resveratrol to a wound through the layers of the epidermis can reduce scar formation. Application of resveratrol to a wound before wound formation or up to 24 hours after wound formation results in re-epithelialization within 24 hours, resulting in an attenuated scar. See U.S. Patent Application Publication No. 2015/0005391 to Cole.

Although it is not known exactly how resveratrol reduces scarring, resveratrol up-regulates and increases the expression of a variety of agents which are involved in wound healing. One possible explanation is that resveratrol causes the over-expression of matrix metalloproteinase-9 (MMP-9), interleukin-8 (IL-8) and SIRT1, and increases expression of epidermal growth factor receptor (EGFR) on the keratinocyte membrane and nucleus. SIRT1 may then promote differentiation, motility and proliferation of keratinocytes, and deacetylation and inactivation of p53 protein, inhibiting p53-dependent cell death from apoptosis in response to stress in human tenocytes (fibroblast-like tendon cells). SIRT1 may induce nitric oxide (NO) production, which inhibits Class I HDAC 2 from blocking growth factors including epithelial growth factor, keratinocyte growth factor 2, fibroblast growth factor 10 (FGF-10) and insulin-like growth factor 1 (IGF-1). SIRT1 may also decrease inflammation and apoptosis through a variety of mechanisms. IL-8 has a direct and profound stimulatory effect on the migration of keratinocytes, which is likely via the PLC-γ pathway. IL-8 may also recruit neutrophils. MMP-9 degrades the Type IV collagen of the basement membrane. EGFR may cause keratinocyte and fibroblast migration and may protect and repair tissue through nuclear DNA repair. Resveratrol may also inhibit NF-κB-dependent pro-inflammatory and matrix-degrading gene products induced by IL-1β and nicotinamide.

SUMMARY

In a first aspect, the invention is a resveratrol ester having the following structure:

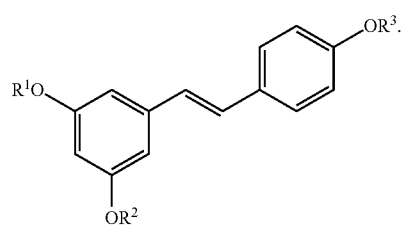

$R^1$, $R^2$ and $R^3$ are H or

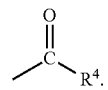

Each $R^4$ is independently a carbon chain of 2 to 4 carbon atoms comprising a terminal carboxylic acid moiety, a carbon chain of 1 to 5 carbon atoms comprising an amine moiety, or

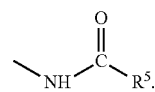

$R^5$ is a carbon chain of 3 or 4 carbon atoms having a terminal carboxylic acid moiety. At least one of $R^1$, $R^2$ and $R^3$ is

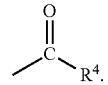

Salts of resveratrol esters are also included.

In a second aspect, the invention is a method of making a resveratrol ester, comprising forming the resveratrol ester from resveratrol.

In a third aspect, the invention is a composition comprising a resveratrol ester and a pharmaceutically acceptable carrier.

In a fourth aspect, the invention is a resveratrol ester selected from the group consisting of resveratrol hemimalonate, resveratrol hemisuccinate, resveratrol hemiglutarate, resveratrol 2-aminopropanoate, resveratrol 2-amino-3-methylbutanoate, resveratrol 2-amino-4-methylpentanoate, resveratrol 2-amino-3-methylpentanoate, resveratrol aminoethanoate, resveratrol 4-(4-aminophenyl)-butyrate, resveratrol 4-amino-butyrate, and resveratrol 6-amino-hexanoate.

In a fifth aspect, the invention is resveratrol trihemiglutarate.

In a sixth aspect, the invention is a method of reducing scar formation, comprising administering an effective amount of a composition comprising a resveratrol ester and a pharmaceutically acceptable carrier to a patient in need thereof.

In a seventh aspect, the invention is a method of making a composition comprising a resveratrol ester and a pharmaceutically acceptable carrier. The method does not include a solvent comprising alcohol.

DEFINITIONS

"Resveratrol esters" include resveratrol esters of carboxylic acids, resveratrol esters of amino acids and amides thereof with dicarboxylic acids. Species of resveratrol esters contain the prefix mono-, di-, or tri- to indicate the number of ester linkages present in the resveratrol ester. The absence of the mono-, di-, or tri-prefix indicates a class containing the three species. For example, resveratrol hemiglutarate refers to the class of resveratrol esters containing the three species resveratrol monohemiglutarate, resveratrol dihemiglutarate, and resveratrol trihemiglutarate.

A "resveratrol precursor" or a "resveratrol prodrug" is a compound that is converted to resveratrol by the body.

"Hydroxyl" (or hydroxy-) refers to an —OH moiety.

"Carboxylic acid" (or carboxy-) refers to a compound with at least one —COOH moiety.

"Dicarboxylic acid" refers to a compound having two carboxylic acid moieties (—COOH).

"Amino acid" refers to a compound having an amine moiety (—NH$_2$) and a carboxylic acid moiety (—COOH).

"Amide" refers to a compound with at least one —(CO)N— moiety.

"Saturated" refers to a compound with no carbon-carbon double or triple bonds.

A "carbonyl carbon" is a carbon atom that is double-bonded to an oxygen atom.

An "ester linkage" refers to the oxygen-carbonyl bond in an ester:

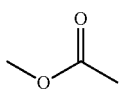

All percentages (%) are weight/weight percentages, unless stated otherwise.

BRIEF DESCRIPTION OF THE DRAWINGS

The invention can be better understood with reference to the following drawings and description.

FIG. 14 is a mass spectrum of resveratrol tri-phenylalaninate obtained by LC/MS.

DETAILED DESCRIPTION

Figure 1:
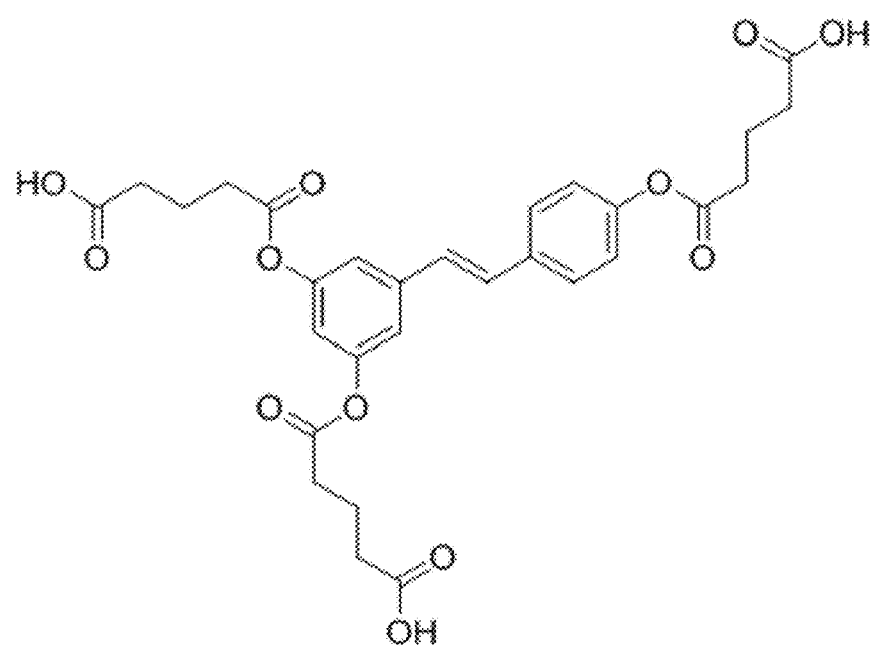
FIG. 1 is the chemical structure of resveratrol trihemiglutarate.

It has been discovered that local administration of resveratrol, such as into a wound, is challenging due to its low solubility in water (0.03 g/L). As a result, a large amount of resveratrol is typically required to deliver a therapeutically effective amount to a target application site. The delivery of resveratrol may be improved by administering a resveratrol precursor having greater water solubility than resveratrol. By increasing the solubility relative to resveratrol, a smaller amount of the resveratrol precursor may be used to deliver a therapeutically equivalent amount of resveratrol. However, if the solubility of the resveratrol precursor is too high, the resveratrol precursor will diffuse away from the target application site and fail to deliver the resveratrol as intended. It is important to avoid diffusion of the resveratrol precursor since resveratrol is applied locally, preferably at the target application site. There is a need for a resveratrol precursor, such as a resveratrol ester, with sufficient water solubility to improve local administration and bioavailability of resveratrol, but not so water soluble so as to diffuse away from the application site.

Another challenge presented by the low solubility of resveratrol is the difficulty in preparing aqueous compositions containing resveratrol. Typically, the preparation of an aqueous composition containing resveratrol involves a two-step process. Resveratrol is first dissolved in an alcohol, such as ethanol. Next, the resveratrol/alcohol solution is dissolved in water to form an aqueous composition. Although this two-step process overcomes the problems presented by the low solubility of resveratrol in water, it is disfavored when the composition containing resveratrol is to be used in the reduction of scarring because alcohols are known fibrotic agents. The amount of alcohol in the aqueous composition containing resveratrol may be reduced, but cannot be completely eliminated. As a result, compositions containing resveratrol prepared by a process involving dissolution in alcohol will contain some amount of a fibrotic agent. There is a need for a method of preparing an aqueous composition containing resveratrol, or a resveratrol precursor, that excludes alcohol.

The present invention makes use of the discovery of resveratrol precursors with greater water solubility and greater bioavailability than resveratrol that are not so water soluble so as to diffuse away from the application site. Resveratrol esters were identified as promising precursor candidates for resveratrol delivery because of the wide availability of esterases in vivo. Applicants have surprisingly discovered that certain resveratrol esters possess unexpected and superior efficacy and bioavailability as compared to resveratrol. The resveratrol esters were found to have increased water solubility while still allowing the resveratrol molecules to enter cells and provide the intended therapeutic benefits. The esters chosen provide increased polarity without being so hydrophilic that the resveratrol precursors diffuse away from the site of application.

The present invention also makes use of the discovery of an improved method for producing aqueous compositions containing resveratrol precursors, such as resveratrol esters. Resveratrol esters have increased water solubility as compared to resveratrol, which allows compositions containing resveratrol esters to be prepared without first dissolving the resveratrol esters in alcohol. The method eliminates the introduction of alcohol, a known fibrotic agent, while also simplifying the production process.

Resveratrol esters may have an ester linkage at any of the three hydroxyl moieties on resveratrol. Resveratrol esters may be formed by any suitable chemical reaction, such as esterification with a dicarboxylic acid or esterification with an amino acid. Resveratrol esters include resveratrol with one, two, or three of the hydroxyl moieties modified by an ester linkage. Preferably, the resveratrol hydroxyl moieties have the same ester linkage when more than one resveratrol hydroxyl moiety is modified.

Resveratrol esters of carboxylic acids have an ester linkage between one or more of the resveratrol hydroxyl moieties oxygens and the carbonyl carbon from the carboxylic acid moiety. Preferably, the carboxylic acid used is a dicarboxylic acid. Dicarboxylic acids are preferred because they retain a carboxylic acid moiety after esterification at the other carboxylic acid moiety. Retention of a carboxylic acid moiety increases the acidity of the resveratrol esters, which in turn increases the solubility of the resveratrol esters. Preferably, the dicarboxylic acid is a linear saturated dicarboxylic acid containing up to 5 carbon atoms. Suitable dicarboxylic acids include malonic acid (propanedioic acid), succinic acid (butanedioic acid) and glutaric acid (pentanedioic acid). A preferred dicarboxylic acid is glutaric acid. It was surprisingly discovered that esters of resveratrol with dicarboxylic acids having greater than 5 carbon atoms, such as adipic acid (hexanedioic acid) ester, are too lipophilic for use in resveratrol delivery. Similarly, esters of resveratrol with monocarboxylic acids, such as acetates, proprionates, and butyrates, have lower water solubility than resveratrol itself and are too lipophilic for use in resveratrol delivery. Preferred resveratrol esters include hemimalonate [—(CO)(CH$_2$)(CO)(OH)], hemisuccinate [—(CO)(CH$_2$)$_2$(CO)(OH)] and hemiglutarate [—(CO)(CH$_2$)$_3$(CO)(OH)]. A preferred hemiglutarate ester of resveratrol is resveratrol trihemiglutarate. The structure of resveratrol trihemiglutarate is shown in FIG. 1. Resveratrol esters of dicarboxylic acids may be formulated as salts, for example, the sodium, potassium, calcium, or magnesium salts.

Resveratrol esters of amino acids have an ester linkage between one or more of the resveratrol hydroxyl moieties oxygens and the carbonyl carbon from the carboxylic acid moiety of the amino acid. If resveratrol esters of amino acids are formed by esterification, the amine moiety must be protected before the carboxylic acid moiety participates in esterification, such as with the tert-butyloxycarbonyl protecting group (boc or t-boc). After esterification, the amine moiety may optionally be de-protected. Resveratrol esters of amino acids are often more stable than resveratrol esters of dicarboxylic acids. Preferably, the amino acid used has a low molecular weight. Suitable natural amino acids include alanine (2-aminopropanoic acid), valine (2-amino-3-methylbutanoic acid), leucine (2-amino-4-methylpentanoic acid), isoleucine (2-amino-3-methylpentanoic acid), glycine (aminoethanoic acid) and phenylalanine (2-amino-3-phenyl-propanoic acid). Suitable non-natural amino acids include 4-(4-aminophenyl)-butyric acid, 4-amino-butyric acid and 6-amino-hexanoic acid. A preferred amino acid is valine. Preferred resveratrol esters formed from natural amino acids include 2-aminopropanoate (alaninate) [—(CO)(NH$_2$)CHCH$_3$], 2-amino-3-methylbutanoate (valinate) [—(CO)CH(NH$_2$)CH(CH$_3$)$_2$], 2-amino-4-methylpentanoate (leucinate) [—(CO)CH(NH$_2$)CH$_2$CH(CH$_3$)$_2$], 2-amino-3-methylpentanoate (isoleucinate) [—(CO)CH(NH$_2$)CH(CH$_3$)CH$_2$CH$_3$], aminoethanoate (glycinate) [—(CO)CH$_2$NH$_2$] and 2-amino-3-phenylpropanoate (phenylalaninate) [—(CO)(NH$_2$)CHCH$_2$C$_6$H$_5$]. Preferred resveratrol esters formed from non-natural amino acids include 4-(4-aminophenyl)-butyrate [—(CO)(CH$_2$)$_3$(C$_6$H$_4$)NH$_2$], 4-amino-butyrate [—(CO)(CH$_2$)$_3$NH$_2$], and 6-amino-hexanoate [—(CO)(CH$_2$)$_5$NH$_2$]. If a protecting group is used, the resveratrol ester may be provided without removing the protecting group, such as resveratrol tri-alaninate-boc. Resveratrol esters of amino acids may be formulated as salts, for example, the hydrochloride salt.

Resveratrol esters of amino acids also include resveratrol esters of amides.

Resveratrol esters of amides may be formed by reacting the amine moiety of a resveratrol ester of an amino acid with a dicarboxylic acid having a carbon chain of 3 or 4 carbon atoms. Suitable dicarboxylic acids include malonic acid (propanedioic acid) and succinic acid (butanedioic acid). Preferred resveratrol esters of amides include N-hemimalonate [—(CO)(CH$_2$)(CO)(OH)] and N-hemisuccinate [—(CO)(CH$_2$)$_2$(CO)(OH)]. Resveratrol esters of amides may be formulated as salts.

A resveratrol ester has the following general structure:

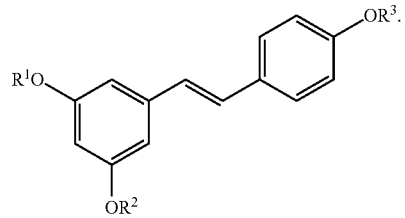

$R^1$, $R^2$, and $R^3$ may be a hydrogen atom (H) or

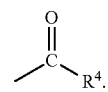

Each $R^4$ is independently a carbon chain of 2 to 4 carbon atoms having a terminal carboxylic acid moiety, a carbon chain of 1 to 5 carbon atoms having an amine moiety, or

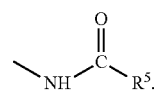

$R^5$ is a carbon chain of 3 or 4 carbon atoms having a terminal carboxylic acid moiety. At least one of $R^1$, $R^2$, and $R^3$ is not H. Each $R^4$ may be substituted or unsubstituted, saturated or unsaturated, and straight or branched. Preferably, each $R^4$ is unsubstituted, saturated and linear. $R^1$, $R^2$, and $R^3$ may be the same, or may be different. The resveratrol esters may optionally be formulated as salts.

The resveratrol esters may be combined with pharmaceutically acceptable excipients or carriers to form compositions containing resveratrol esters that may be applied therapeutically. Preferably, the compositions containing resveratrol esters are administered by injection or topically. For example, a composition containing resveratrol esters may be administered topically as a lotion, ointment, cream, gel, paste, foam, suspension, topical solution or other suitable topical form. Preferably, the compositions containing resveratrol esters are sterile.

Compositions containing resveratrol esters are preferably prepared without first dissolving the resveratrol esters in alcohol. Resveratrol esters may be dissolved in emulsifiers and solubilizers that do not contain alcohol. Suitable solvents include emulsifiers and solubilizers in the KOLLIPHOR® portfolio produced by BASF. A preferred solvent is KOLLIPHOR® ELP.

Compositions containing resveratrol esters may optionally contain agents that do not materially affect the basic and novel characteristics of the resveratrol esters. For example, compositions containing resveratrol esters may optionally include agents such as stabilizers, preservatives or pH adjusters. If the compositions containing resveratrol esters are administered topically, the pH of the compositions must be carefully chosen to deliver the ester in its intended form without being irritating to the skin or tissue. Preferably, the pH of compositions containing resveratrol esters that are administered topically is 4.0-7.0 to closely match the pH of normal skin.

Preferably, the resveratrol esters are present in a composition at a concentration of at least 0.1 micromoles/liter, more preferably at a concentration of at least 1.0 micromoles/liter, and most preferably at a concentration of at least 5.0 micromoles/liter. Preferably, the resveratrol esters are present in those compositions at a concentration of at most 1000 micromoles/liter. Examples include 7.5, 8.0, 9.0, 10, 12.5, 15, 16, 17, 18, 19, 20, 21, 21.9, 22, 23, 24, 25, 26, 27, 28, 29, 30, 32.5, 35, 37.5, 40, 42.5, 45, 47.5, 50, 55, 60, 65, 70, 75, 80, 90, 100, 150, 200, 250, 300, 350, 400, 450 and 500 micromoles/liter.

Premeasured amounts of the compositions containing resveratrol esters may also be used. These are referred to as unit dosage forms, since each premeasured amount is intended to be used on a single patient for one or more application, all used at the same time. Examples include prefilled syringes, pouches, packets and tubes. Another example is a tube or dispenser which may be used to form foam of its contents just prior to application, for example by shaking or using a foaming agent. A self-foaming tablet, which forms foam when placed into water, could also be used. The volume of material present in these unit dosage forms may be 0.1 to 100 mL, or 1 to 50 mL, including 2, 3, 4, 5, 6, 7, 8, 9, 10, 11, 12, 13, 14, 15, 20, 25, 30, 35, 40 and 45 mL.

A list of exemplary resveratrol esters is given in Table A:
Table A
resveratrol monohemimalonate
resveratrol dihemimalonate
resveratrol trihemimalonate
resveratrol monohemisuccinate
resveratrol dihemisuccinate
resveratrol trihemisuccinate
resveratrol monohemiglutarate
resveratrol dihemiglutarate
resveratrol trihemiglutarate
resveratrol mono-2-aminopropanoate
resveratrol di-2-amino-3-methylbutanoate
resveratrol tri-2-amino-4-methylpentanoate
resveratrol mono-2-amino-3-methylpentanoate
resveratrol di-aminoethanoate
resveratrol tri-4-(4-aminophenyl)-butyrate
resveratrol mono-4-amino-butyrate
resveratrol di-6-amino-hexanoate

EXAMPLES

Example 1

Resveratrol Trihemiglutarate Synthesis

The following scheme depicts the process of preparing the trihemiglutarate ester of resveratrol:

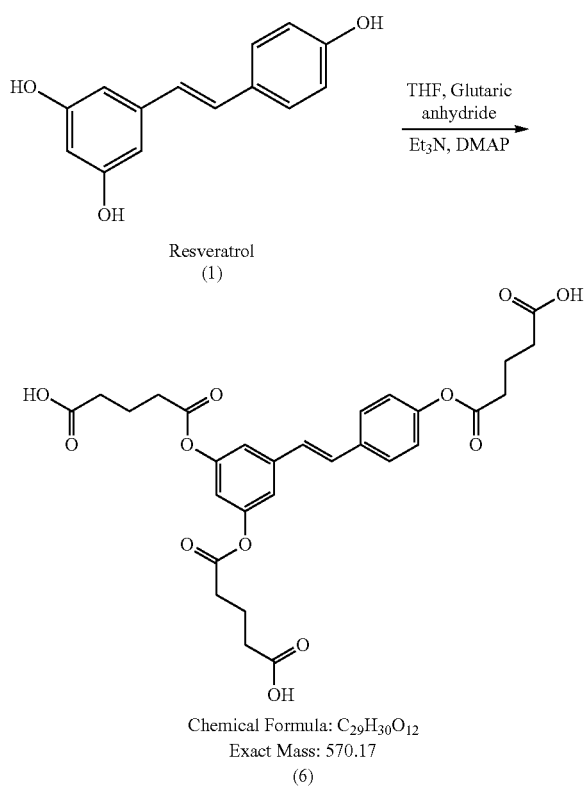

Resveratrol (1) 2 g, (Combi-Blocks, Inc., CR-1053, batch# A83528) was dissolved in 50 mL tetrahydrofuran (THF). 75 mg of 4-dimethylaminopyridine (DMAP) was added to the solution while stirring at room temperature. 0.8 mL triethylamine (Et$_3$N) (Sigma-Aldrich, T0886, batch #126K07554) and 3.32 g glutaric anhydride (Sigma-Aldrich, G3806, batch #0418JB) were added to the stirring solution of resveratrol. The reaction was allowed to stir overnight. In the morning TLC (using 50% ethyl acetate in hexanes as the solvent system with a spray reagent composed of 5% sulfuric acid in methanol, heat) against starting material indicated disappearance of starting material and appearance of a new polar spot. The solvent of the reaction mixture was evaporated to produce a semi-solid gum. This semi-solid gum was separated by chromatography on silica gel (60% ethyl acetate in hexanes with 0.1% trifloroacetic acid) and pure resveratrol trihemiglutarate (6) was obtained after combining the pure fractions (2.12 g).

Figure 2:
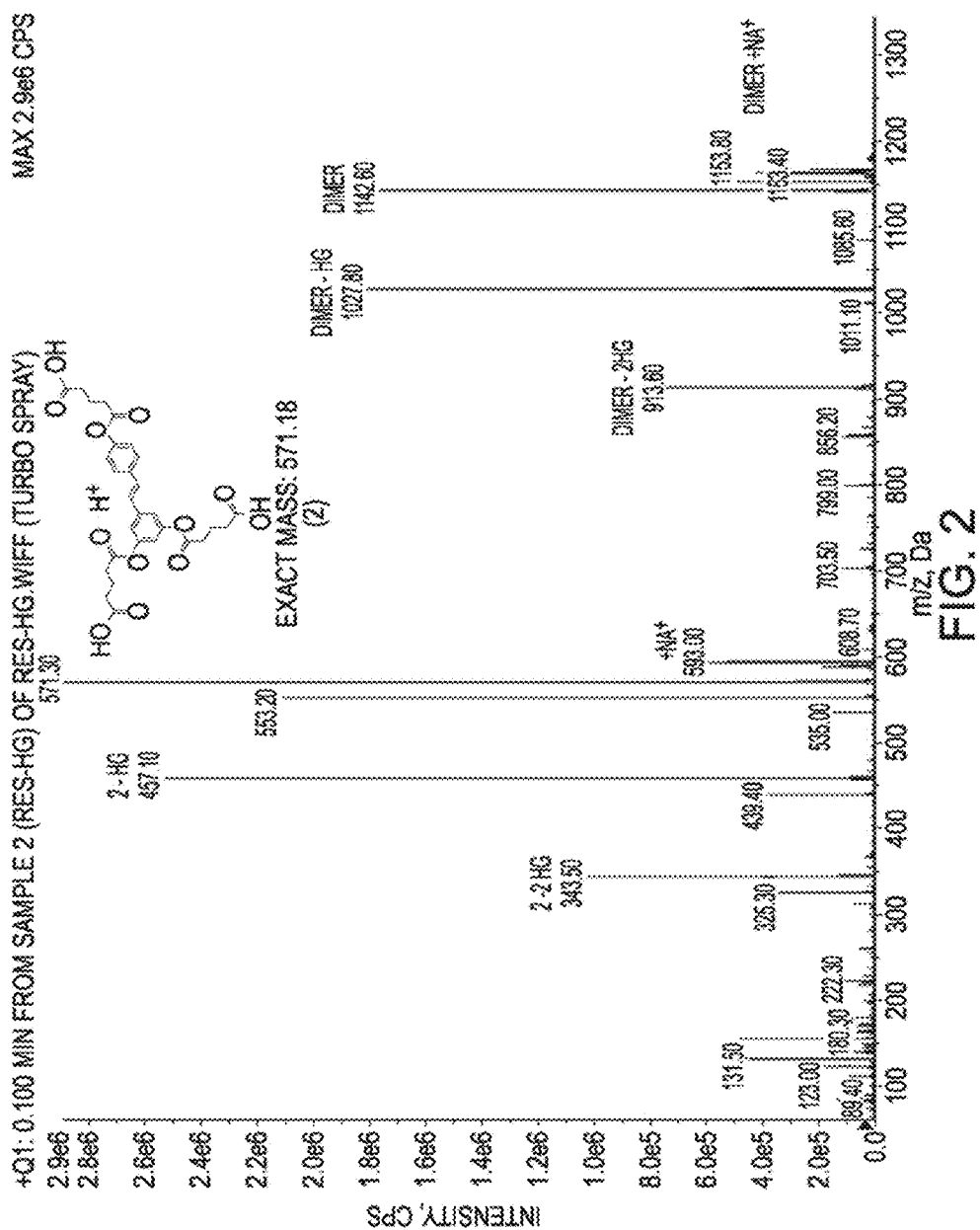
FIG. 2 is a mass spectrum of resveratrol trihemiglutarate obtained by LC/MS.

The mass of the resveratrol trihemiglutarate product (6) was confirmed by LC/MS. The mass spectrum is shown in FIG. 2.

Figure 3A:
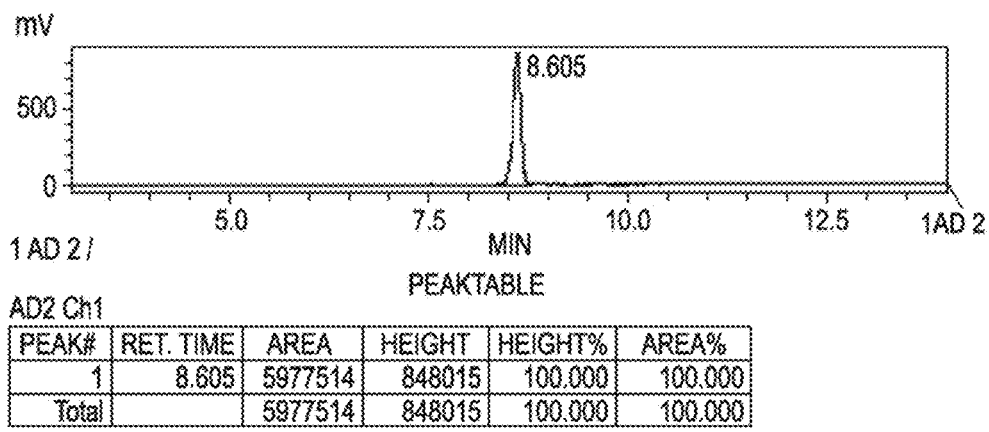
FIG. 3A is a chromatogram of resveratrol obtained by HPLC in units of millivolts (mV) using an evaporative light scattering detector (ELSD).
Figure 3B:
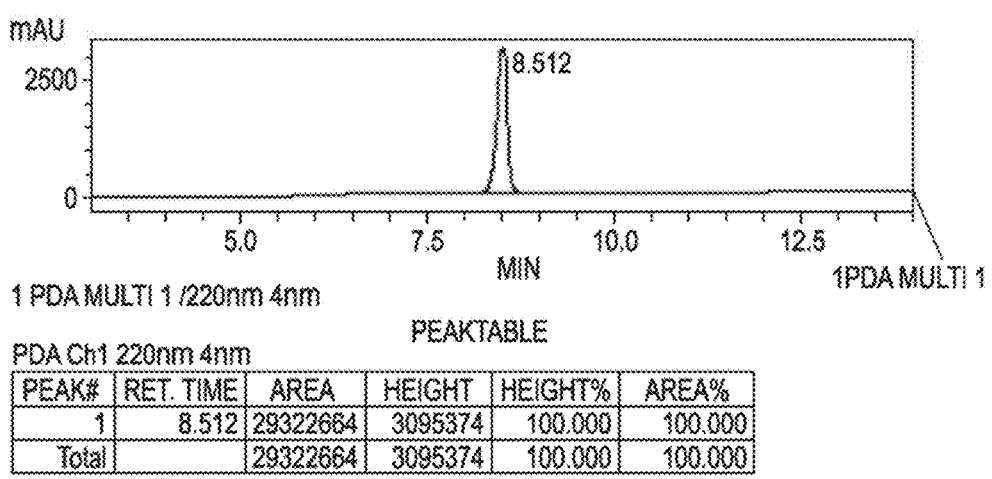
FIG. 3B is a chromatogram of resveratrol obtained by HPLC in units of milli absorbance units (mAU) using a UV detector.
Figure 4A:
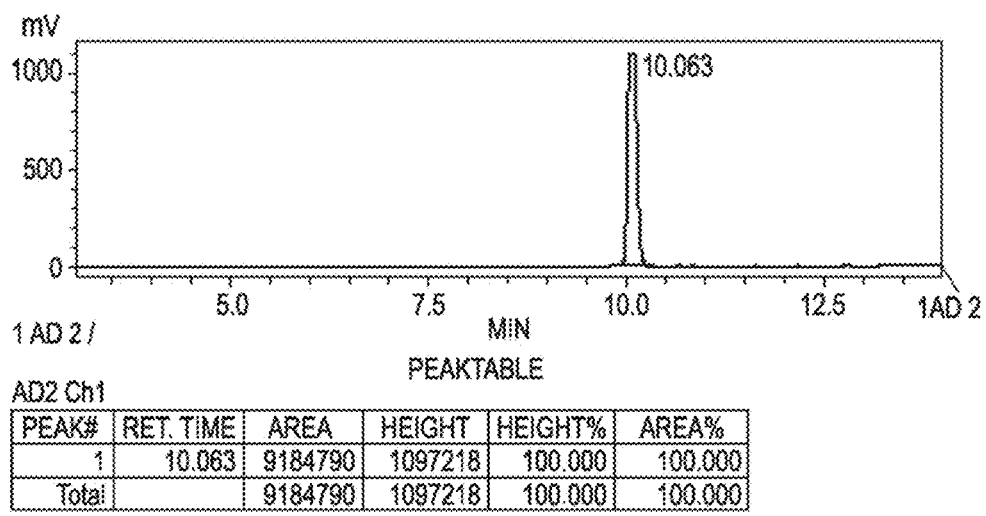
FIG. 4A is a chromatogram of resveratrol trihemiglutarate obtained by HPLC in units of millivolts (mV) using an ELSD.
Figure 4B:
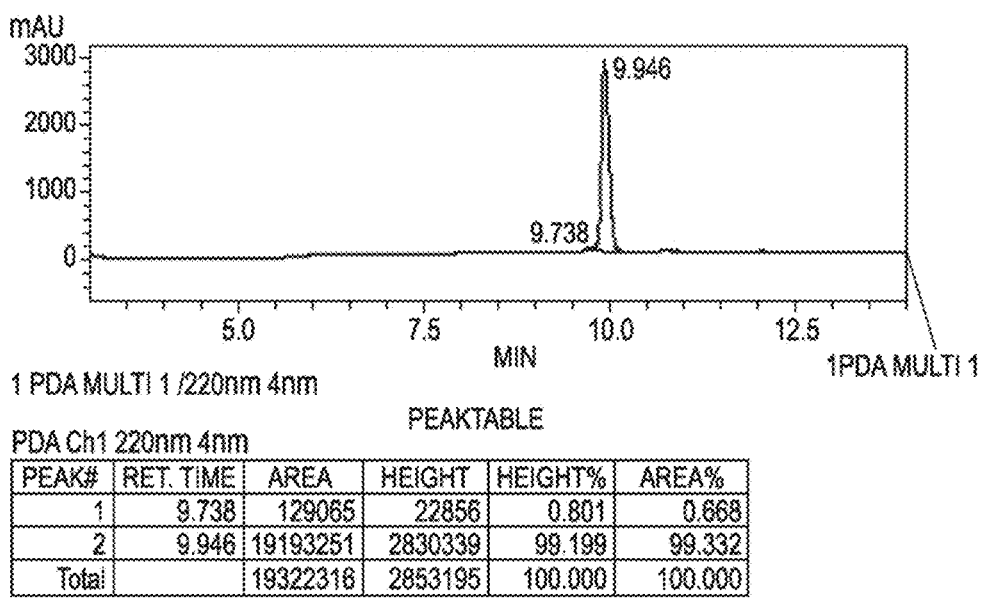
FIG. 4B is a chromatogram of resveratrol trihemiglutarate obtained by HPLC in units of milli absorbance units (mAU) using a UV detector.

The resveratrol starting material (1) and the resveratrol trihemiglutarate product (6) were analyzed by HPLC. Chromatograms were obtained using an evaporative light scattering detector (ELSD) and a UV detector. FIG. 3A is a chromatogram of resveratrol (1) obtained using an ELSD. FIG. 3B is a chromatogram of resveratrol (1) obtained using a UV detector. FIG. 4A is a chromatogram of resveratrol trihemiglutarate (6) obtained using an ELSD. FIG. 4B is a chromatogram of resveratrol trihemiglutarate (6) obtained using a UV detector.

Example 2

Resveratrol Trihemisuccinate Synthesis

Resveratrol was dissolved in tetrahydrofuran (THF). 4-dimethylaminopyridine (DMAP) was added to the solution while stirring. Succinic anhydride and triethylamine ($Et_3N$) were added to the stirring solution of resveratrol to produce crude resveratrol trihemisuccinate. The resveratrol trihemisuccinate was loaded onto a silica gel column packed in hexanes. The product was brought down beginning with 10% ethyl acetate (EtOAc)/90% hexane with 0.1% trifluoroacetic acid (TFA). Fractions were collected and tested by thin layer chromatography for purity. Similar fractions containing pure product were combined.

Figure 6:
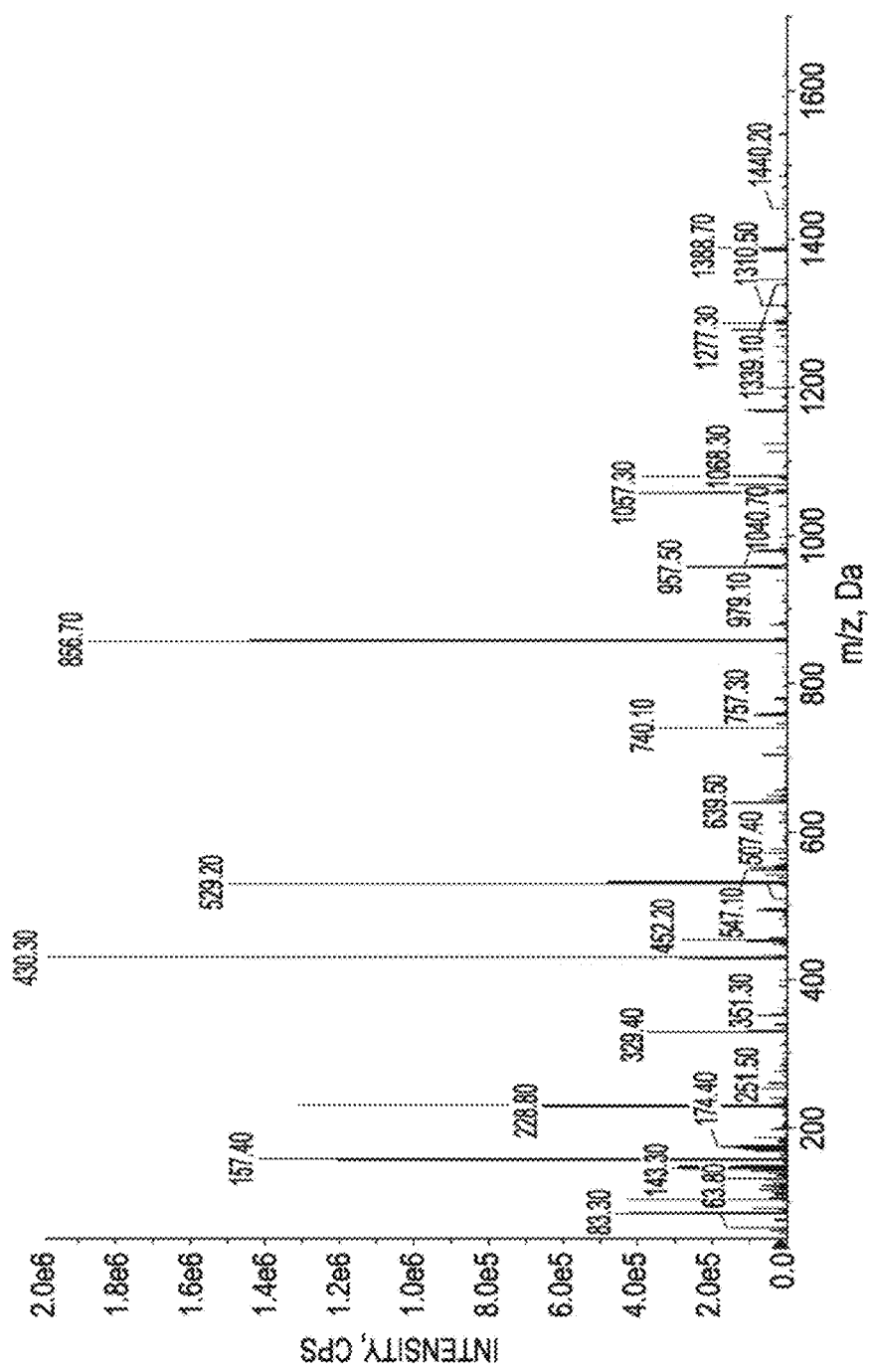
FIG. 6 is a mass spectrum of resveratrol trihemisuccinate obtained by LC/MS.

The mass of the resveratrol trihemisuccinate product was confirmed by LC/MS. The mass spectrum is shown in FIG. 6.

Example 3

Resveratrol Tri-alaninate-boc Synthesis

Resveratrol was dissolved in dichloromethane (DCM). 4-dimethylaminopyridine (DMAP) was added to the solution while stirring. In a separate flask, boc-β-alanine hydroxide and dicyclohexylcarbodiimide (DCC) were dissolved in dichloromethane. The resveratrol solution and the alanine solution were combined while stirring to produce crude resveratrol tri-alaninate-boc. The crude resveratrol tri-alaninate-boc was dissolved in dichloromethane/ethyl acetate and loaded onto a silica gel column packed in hexanes. The product was brought down with a step gradient beginning at 100% hexane and increasing ethyl acetate until reaching 50% hexane/50% ethyl acetate. Fractions were collected and tested by thin layer chromatography for purity. Similar fractions containing pure product were combined.

Figure 7:
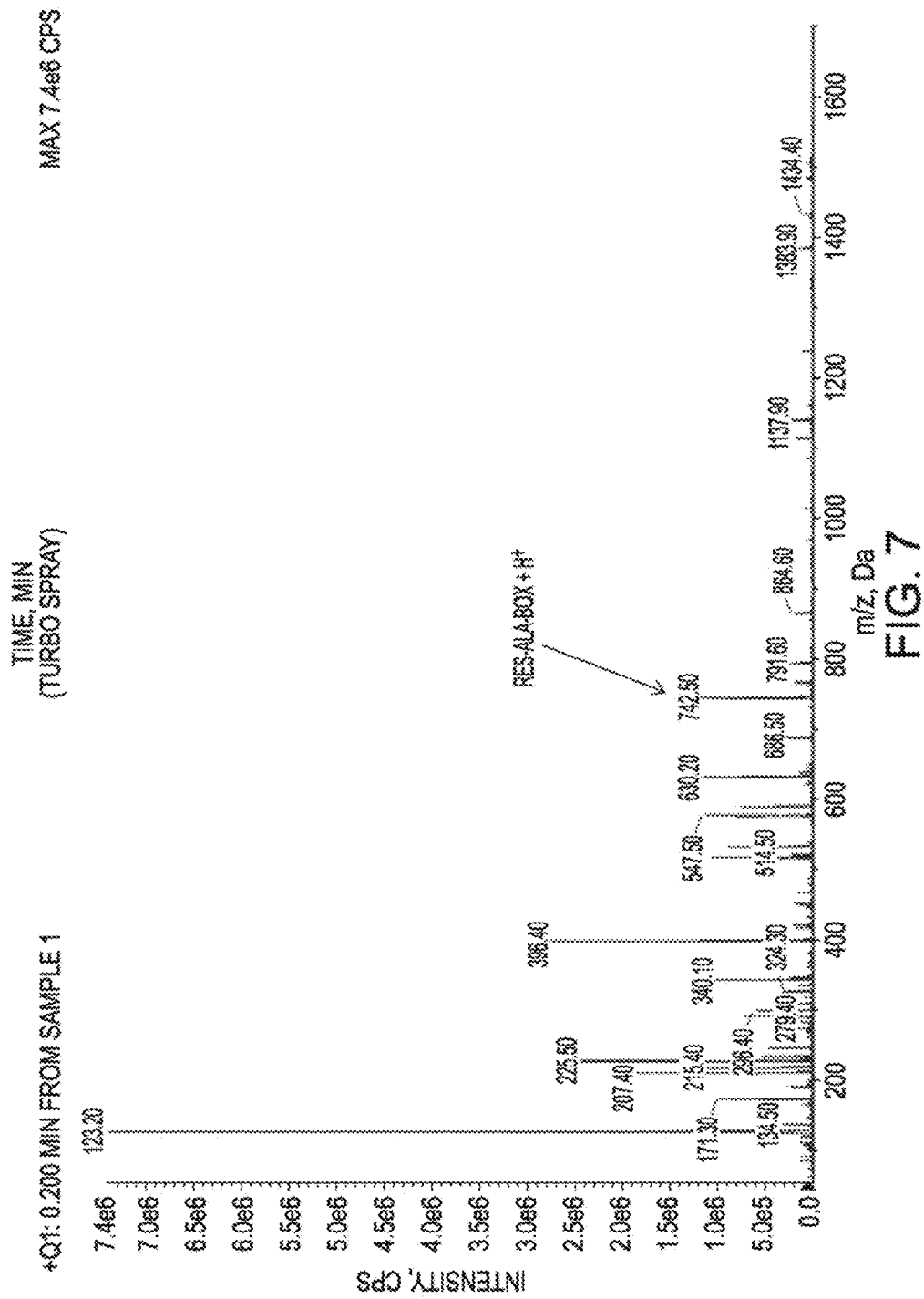
FIG. 7 is a mass spectrum of resveratrol tri-alaninate-boc obtained by LC/MS.

The mass of the resveratrol tri-alaninate-boc product was confirmed by LC/MS. The mass spectrum is shown in FIG. 7.

Example 4

Resveratrol Tri-alaninate HCl Synthesis

Resveratrol tri-alaninate-boc was prepared according to Example 3. The resveratrol tri-alaninate-boc was then dissolved in tetrahydrofuran (THF). Hydrochloric acid (HCl) gas was bubbled through the solution at room temperature while stirring. A white precipitate was formed, resveratrol tri-alaninate HCl, and was filtered to produce a pure product.

Figure 8:
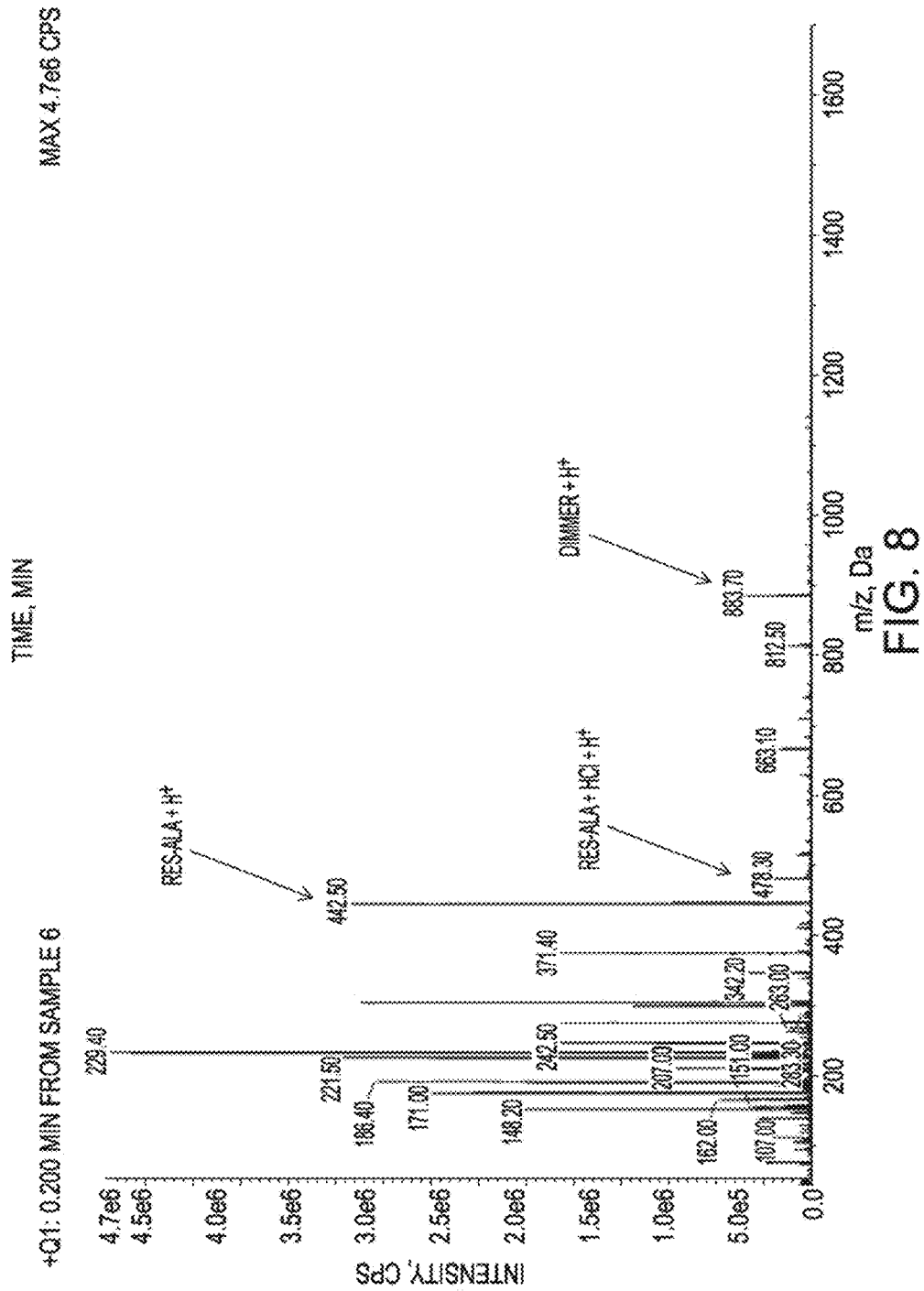
FIG. 8 is a mass spectrum of resveratrol tri-alaninate HCl obtained by LC/MS.

The mass of the resveratrol tri-alaninate HCl product was confirmed by LC/MS. The mass spectrum is shown in FIG. 8.

Example 5

Resveratrol Mono-, Di-, and Tri-valinate-boc Synthesis

Resveratrol was dissolved in tetrahydrofuran (THF). 4-dimethylaminopyridine (DMAP) was added to the solution while stirring. In a separate flask, boc-valine hydroxide and dicyclohexylcarbodiimide (DCC) were dissolved in tetrahydrofuran while stirring. The resveratrol solution and the valine solution were combined while stirring to produce crude resveratrol valine-boc. The crude resveratrol valine-boc was dissolved in dichloromethane/hexane and loaded onto a silica gel column packed in hexanes. The product was brought down with a step gradient beginning at 100% hexane (with 0.1% trifluoroacetic acid (TFA)) and increasing ethyl acetate until reaching 60% hexane/40% ethyl acetate (with 0.1% TFA). Fractions were collected and tested by thin layer chromatography (TLC) for purity. Optimal separation on TLC plates occurred in 40% ethyl acetate/60% hexane with 0.1% TFA. TLC showed three products: Resveratrol mono-valinate-boc, resveratrol di-valinate-boc, and resveratrol tri-valinate-boc. Similar fractions containing pure product were combined. Some fractions containing mixtures of products were ran on additional silica gel columns under the same conditions.

Figure 9:
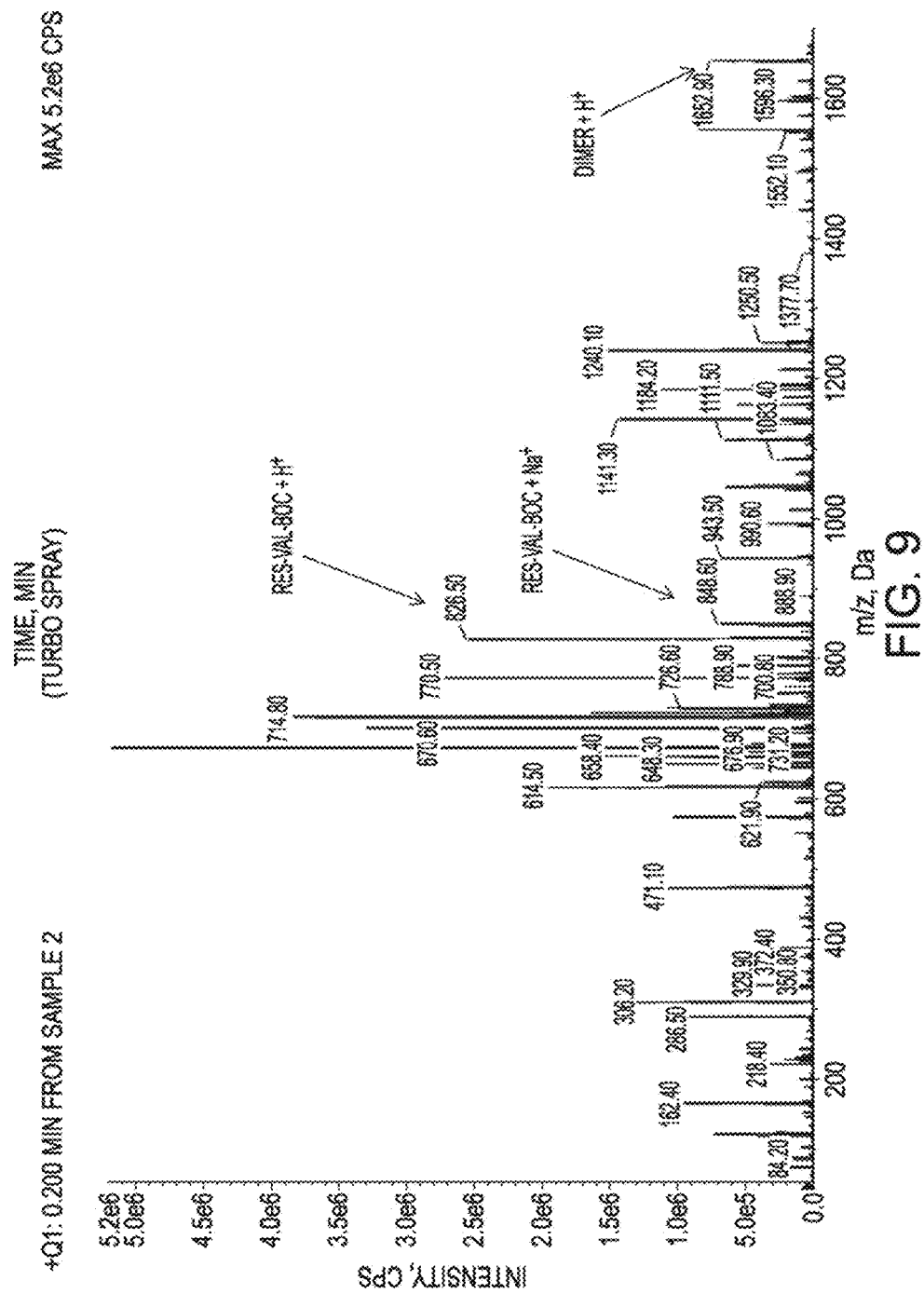
FIG. 9 is a mass spectrum of resveratrol tri-valinate-boc obtained by LC/MS.

The mass of the resveratrol tri-valinate-boc product was confirmed by LC/MS. The mass spectrum is shown in FIG. 9.

Figure 10:
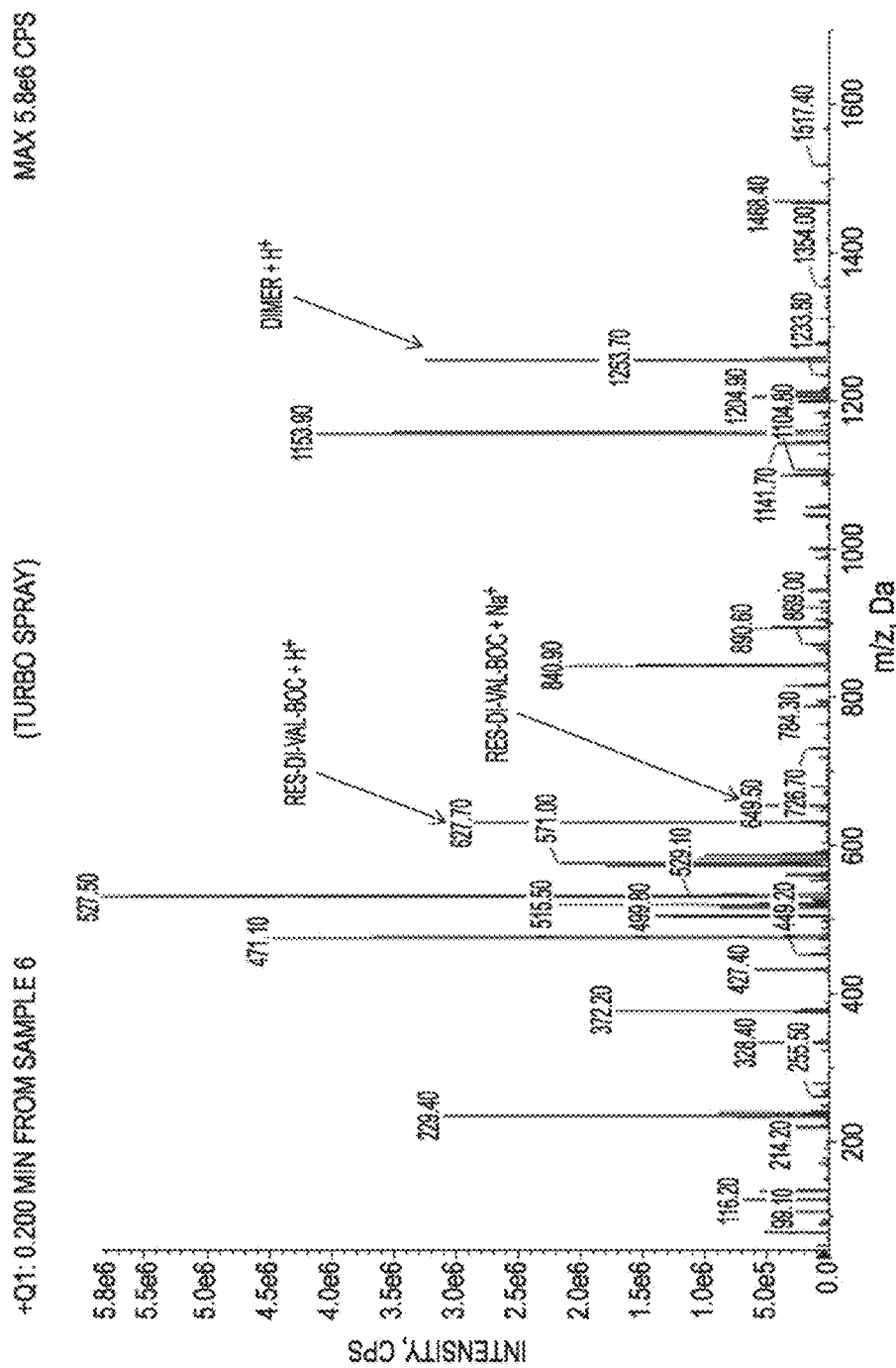
FIG. 10 is a mass spectrum of resveratrol di-valinate-boc obtained by LC/MS.

The mass of the resveratrol di-valinate-boc product was confirmed by LC/MS. The mass spectrum is shown in FIG. 10.

Figure 11:
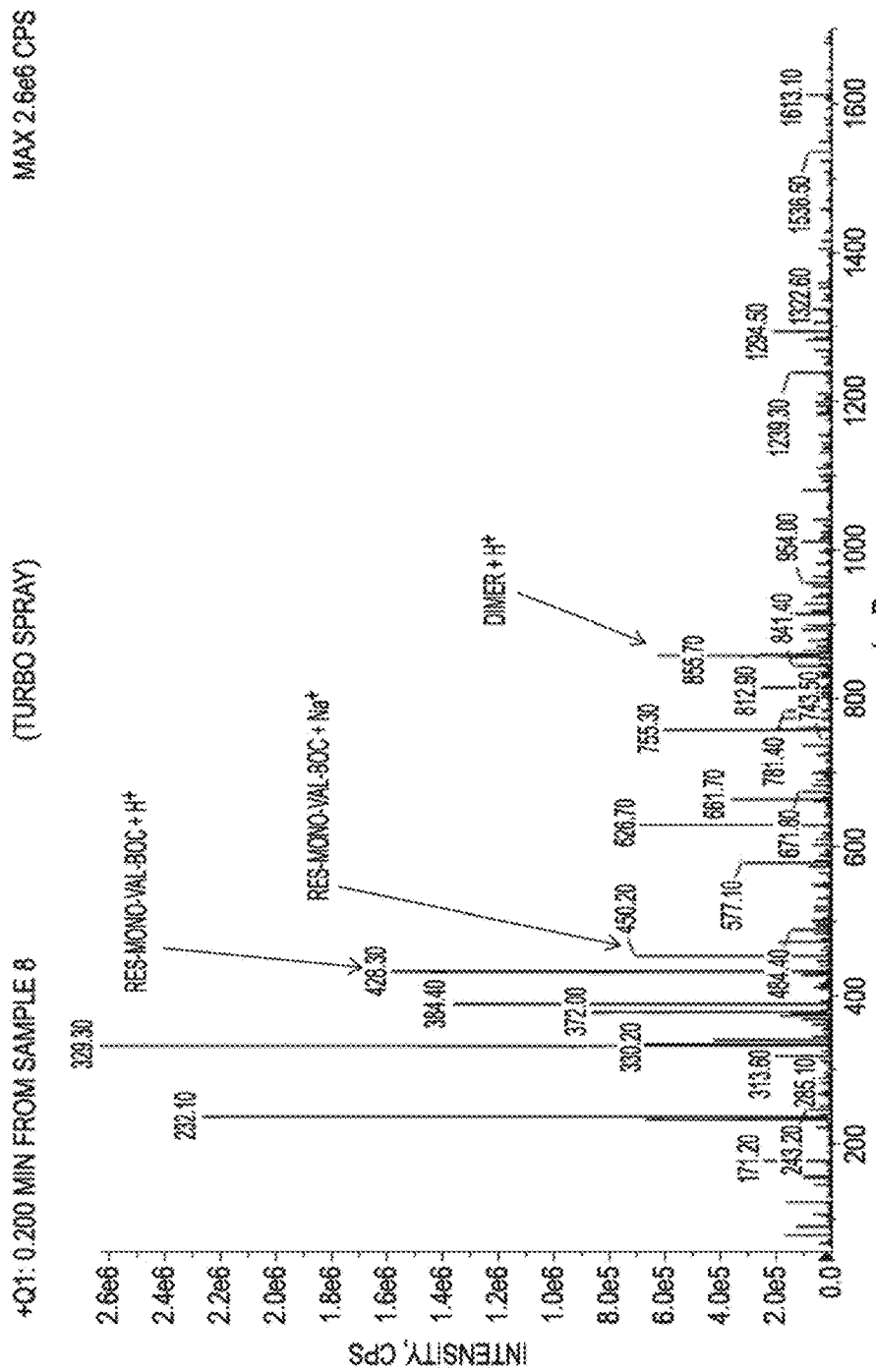
FIG. 11 is a mass spectrum of resveratrol mono-valinate-boc obtained by LC/MS.

The mass of the resveratrol mono-valinate-boc product was confirmed by LC/MS. The mass spectrum is shown in FIG. 11.

Example 6

Resveratrol Tri-valinate HCl Synthesis

Resveratrol tri-valinate-boc was prepared according to Example 5. The resveratrol tri-valinate-boc was then dissolved in tetrahydrofuran (THF). Hydrochloric acid (HCl) gas was bubbled through the solution at room temperature while stirring. A white precipitate was formed, resveratrol tri-valinate HCl, and was filtered to produce a pure product.

Figure 12:
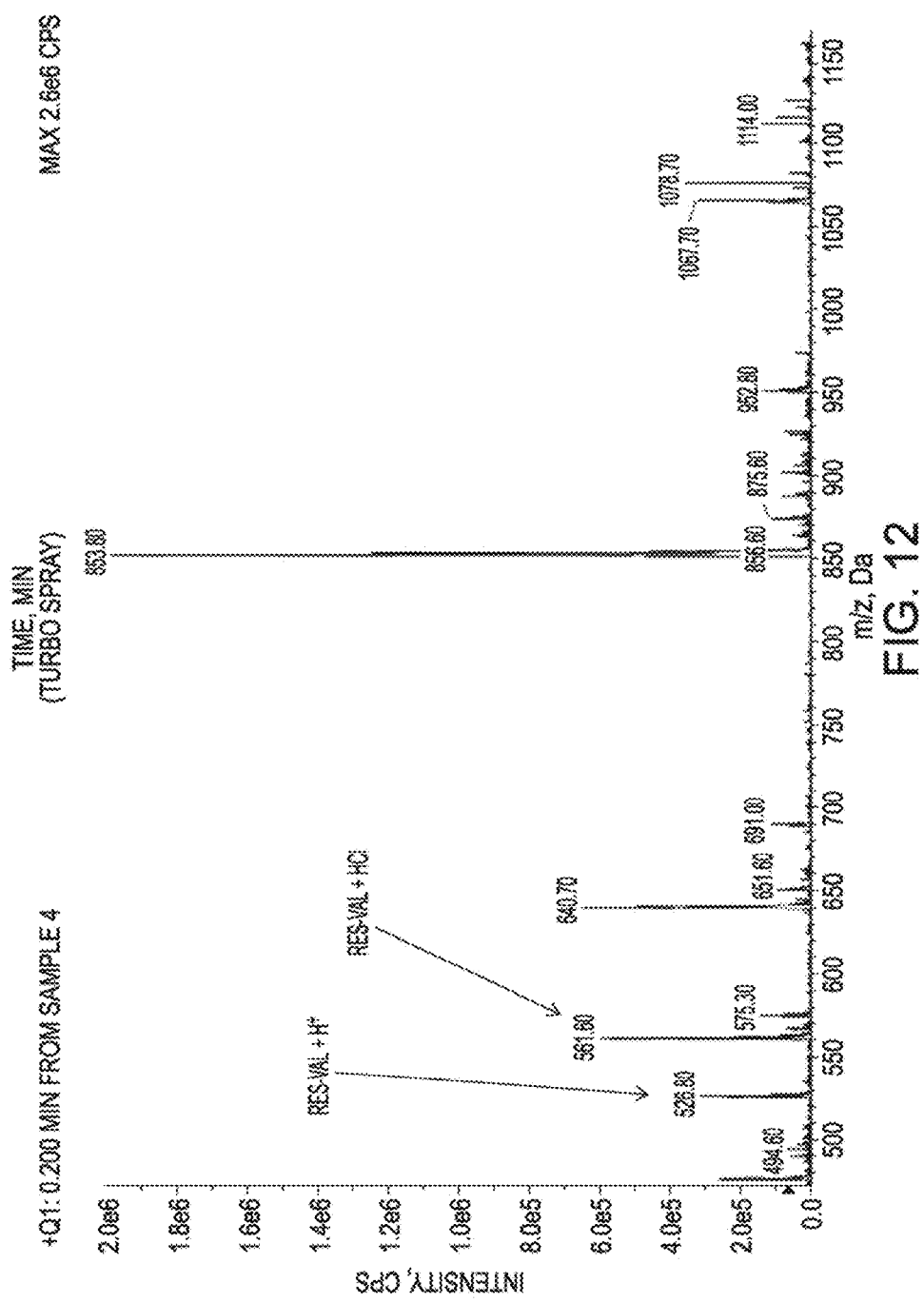
FIG. 12 is a mass spectrum of resveratrol tri-valinate HCl obtained by LC/MS.

The mass of the resveratrol tri-valiante HCl product was confirmed by LC/MS. The mass spectrum is shown in FIG. 12.

Example 7

Resveratrol Tri-valinate-hemisuccinate Synthesis

Resveratrol tri-valinate was dissolved in dichloromethane (DCM). 4-dimethylaminopyridine (DMAP) was added to the solution while stirring. Succinic anhydride and triethylamine ($Et_3N$) were added to the stirring solution of resveratrol to produce crude resveratrol tri-valinate-hemisuccinate. The crude resveratrol tri-valinate-hemisuccinate was loaded (in DCM) onto a silica gel column packed in hexanes. The product was brought down in step gradient beginning with 30% ethyl acetate (EtOAc)/70% hexane, slowly increasing to 100% ethyl acetate, then adding 5% acetonitrile/95% ethyl acetate and increasing to 80% acetonitrile/20% ethyl acetate. 0.1% trifluoroacetic acid was added in the solvent system for the entire separation. Fractions were collected and tested by thin layer chromatography for purity. Similar fractions containing pure product were combined.

Figure 13:
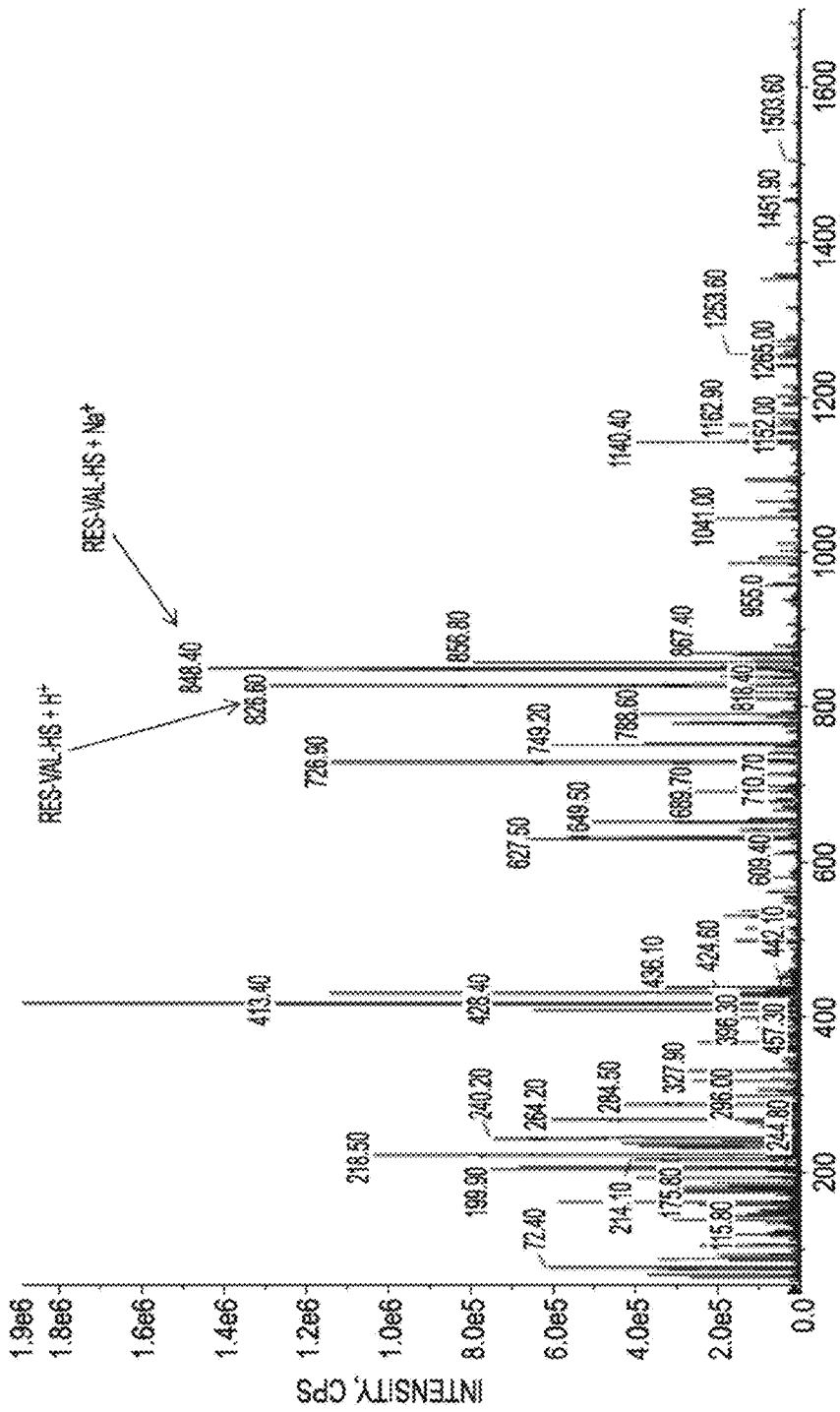
FIG. 13 is a mass spectrum of resveratrol tri-valinate-hemisuccinate obtained by LC/MS.

The mass of the resveratrol tri-valinate-hemisuccinate product was confirmed by LC/MS. The mass spectrum is shown in FIG. 13.

Example 8

Resveratrol Tri-phenylalaninate Synthesis

Resveratrol and 4-dimethylaminopyridine (DMAP) were dissolved in tetrahydrofuran (THF) while stirring. In a separate flask, boc-phenylalanine and dicyclohexylcarbodi-imide (DCC) were dissolved in tetrahydrofuran while stirring. The resveratrol solution and the phenylalanine solution were combined while stirring. The reaction formed a precipitate containing crude resveratrol tri-phenylalaninate-boc, which was vacuum filtered. The filtered product was loaded in dichloromethane onto a silica gel column packed with hexane. The product was brought down in step gradient beginning with 2% ethyl acetate (EtOAc)/98% hexane, slowly increasing to 15% ethyl acetate/85% hexane. Fractions were tested by thin layer chromatography for purity. Similar fractions containing pure product were combined. The sample containing pure fractions of resveratrol tri-phenylalaninate-boc was dissolved in THF while stirring. Hydrochloric acid (HCl) gas was then bubbled through the solution while stirring. A white precipitate was formed, which was vacuum filtered after completion of the reaction. The precipitate was washed with THF, leaving pure resveratrol tri-phenylalaninate.

Figure 14:
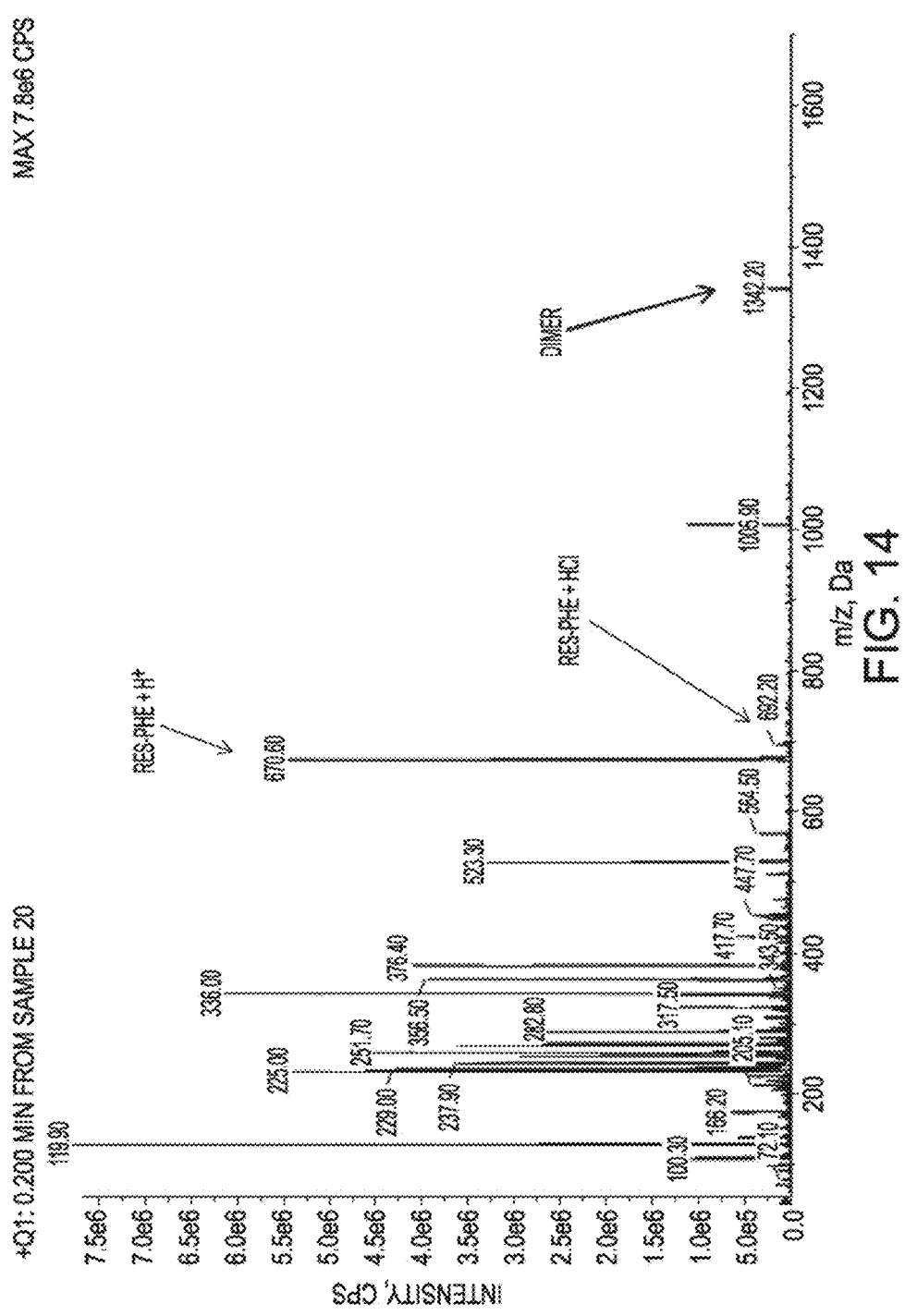

The mass of the resveratrol tri-phenylalaninate product was confirmed by LC/MS. The mass spectrum is shown in FIG. 14.

Example 9

Comparative Solubility

The solubility of resveratrol, resveratrol trihemiglutarate, resveratrol trihemisuccinate, resveratrol tri-valinate-hemisuccinate, resveratrol tri-valinate, resveratrol di-valinate and resveratrol tri-phenylalaninate was compared. Two 4 mg samples of each compound were weighed.

The first sample was used to determine solubility. The sample was mixed with 1 mL of pH 7.4 phosphate buffered saline (PBS) buffer solution to produce a 4 mg/mL solution. The solution was vortexed and filtered to remove undissolved particles. The filtered solution was then diluted in pH 7.4 buffer in triplicate and stored in a refrigerator to reduce hydrolysis. The solutions were allowed to sit at room temperature for 5 minutes and then were analyzed by HPLC.

The second sample was used to prepare a calibration curve in ethanol. Calibrators were made based on expected solubility. After visually inspecting solubility in the buffer, the calibration curve was determined in order to include points above and below the expected concentration. The calibrators were stored in a refrigerator until ready for analysis by HPLC.

The results of the solubility study are as follows:

| Compound | Solubility |
| --- | --- |
| Resveratrol | 0.0048 mg/mL |
| Resveratrol trihemiglutarate | 2.06 mg/mL |
| Resveratrol trihemisuccinate | 0.291 mg/mL |
| Resveratrol tri-valinate-hemisuccinate | 0.201 mg/mL |
| Resveratrol tri-valinate | Not soluble |
| Resveratrol di-valinate | Not soluble |
| Resveratrol tri-phenylalaninate | Not soluble |

Several of the compounds hydrolyzed too quickly to be analyzed by HPLC. Resveratrol trihemiglutarate and resveratrol tri-valinate-hemisuccinate slightly hydrolyzed to the mono- and di-substituted compounds. Resveratrol tri-hemisuccinate experienced quick hydrolysis and was quantitated without resveratrol.

Resveratrol trihemiglutarate was found to have the highest solubility and was approximately 400 times more soluble than resveratrol. Resveratrol trihemisuccinate and resveratrol tri-valinate-hemisuccinate also showed an improved solubility as compared to resveratrol. Although resveratrol tri-valinate, resveratrol di-valinate and resveratrol tri-phenylalaninate were insoluble at pH 7.4, these compounds were expected to be freely soluble at pH 4.0 or less.

Example 10

General Synthesis of Resveratrol Esters Formed from Amino Acids

Resveratrol is dissolved in THF. Di-tert-butyl dicarbonate is added to an amino acid under aqueous conditions to protect the amine group. DMAP is added to the resveratrol while stirring at room temperature. Triethylamine and the protected amino acid are added to the stirring solution of resveratrol and allowed to stir overnight. In the morning, the amine group is de-protected with a strong acid. Thin-layer chromatography is used to verify disappearance of starting material and appearance of a new polar spot. The solvent of the reaction mixture is evaporated. This product is separated by chromatography on silica gel to isolate the desired amino acid ester product.

Example 11

Preparation of a Composition Containing 100 µM Resveratrol Trihemiglutarate

A composition for topical administration was prepared by mixing the following ingredients:
Resveratrol trihemiglutarate—100 µM
Calcium chloride—0.3 mM
Magnesium chloride—3.3 mM
Hydroxypropyl methylcellulose (HPMC) Gel 8%
The composition delivered resveratrol to a wound and improved the healing process in a subject.

Example 12

Preparation of 150 µM Resveratrol Ester Solution

A 150 µM solution of resveratrol trihemiglutarate was prepared. First, 9.975 mg of resveratrol trihemiglutarate powder was accurately weighed. Next, the 9.975 mg of resveratrol trihemiglutarate powder was dissolved in 5 mL of a 25% KOLLIPHOR® ELP solution. The resveratrol trihemiglutarate solution was then filtered into a sterile vial.

Example 13

In Vivo Application of Various Compositions Containing Resveratrol or Resveratrol Esters in a Rat Model 12 Sprague-Dawley rats were placed randomly into 6 different groups, Study Groups 1-6, resulting in 2 animals per study group. Animals were anesthetized and the dorsal subscapular areas were shaved of hair with electric trimmers. Demarcations were made in a gently widening parallel approximately 1 cm subscapular and 2.2 cm in length. The left subscapular incision served as a control and the right subscapular incision served as the treatment site. The subscapular areas were incised with a #15 blade though the skin and subcutaneous panniculus carnosus muscle. The composition mixture corresponding to each group was then instilled into the right subscapular wound and the incision closed with 5-0 nylon interrupted fashion. Additional mixture was applied to the surface of the treatment site incision. Three biopsies were taken of normal skin at the time of incision and prior to any mixture installation. Each site was then monitored and photographed daily. Wound gross morphology was noted daily. Sutures were removed and biopsies were taken at day 8 of the study (postoperative day #7) and sent to pathology for histology review. Histology was reviewed independently by two dermatopathologists.

The Compositions of Study Groups 1-6 were: (1) $Ca^{++}$/$Mg^{++}$/siRNA (MCP-1 inhibitor)/hyaluronic acid tetramer in 8% hydroxypropyl methyl cellulose gel; (2) 100 µM resveratrol trihemiglutarate in 8% hydroxypropyl methyl cellulose gel; (3) 400 µM resveratrol trihemiglutarate in 8% hydroxypropyl methyl cellulose gel; (4) 100 µM resveratrol/$Ca^{++}$/$Mg^{++}$/siRNA (MCP-1 inhibitor)/hyaluronic acid tetramer in 8% hydroxypropyl methyl cellulose gel; (5) 100 µM resveratrol trihemiglutarate/$Ca^{++}$/$Mg^{++}$/siRNA (MCP-1 inhibitor)/hyaluronic acid tetramer in 8% hydroxypropyl methyl cellulose gel; and (6) 200 µM resveratrol trihemiglutarate/$Ca^{++}$/$Mg^{++}$/siRNA (MCP-1 inhibitor)/hyaluronic acid tetramer in 8% hydroxypropyl methyl cellulose gel. A siRNA (MCP-1 inhibitor)

The specimens in Group 1 demonstrated poor re-epithelialization. One specimen experienced dehiscence at the superior pole of the treatment site as well as increased crusting until day 5 with resulting depression at the treatment site. The results suggest that resveratrol is necessary for rapid mobilization of the epithelial keratinocytes. Histology review indicated the largest treatment site dermis fibrosis compared to the control. Mononuclear dermis infiltration was 25% higher in the treatment site. There was moderate to severe evidence of trichogranuloma in all histology specimens.

The specimens in Groups 2 and 3 were compared to previous studies that involved treatment with natural resveratrol. Similar results were noted for 100 µM resveratrol trihemiglutarate as compared to 100 µM natural resveratrol but the resveratrol trihemiglutarate demonstrated mild evidence of trichogranuloma in each of the histology specimens. Earlier studies of 400 µM natural resveratrol showed inflammation and erythema at the treatment site 48 hours post-incision and a similar response was seen in the 400 µM resveratrol trihemiglutarate. There were no differences in histology between control and treatment site at either dosage. The study showed no appreciable difference in treatment between resveratrol trihemiglutarate alone as compared to natural resveratrol alone.

A comparison of Group 4 treatment sites and control sites showed no difference in fibrosis or monocytes at 3 days. However, one specimen died 36 hours postoperatively due to pulmonary embolism. The remaining specimen showed an increase in dermis fibrosis in the resveratrol treatment at 8 days. The death of one specimen limited a full comparison.

A comparison of Group 5 treatment sites and control sites showed no significant difference in re-epithelialization rate or dermal mononuclear infiltrates. The histology comparison noted a 25% increase in panniculus mononuclear infiltrates in the treatment site. As compared to Group 4, Group 5 showed a slightly increased dermal mononuclear infiltrate.

Figure 5A:
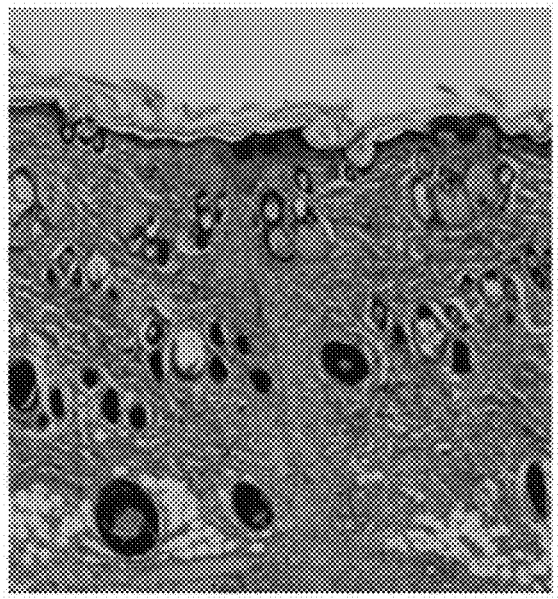
FIG. 5A is a microscopic image of untreated wound tissue.
Figure 5B:
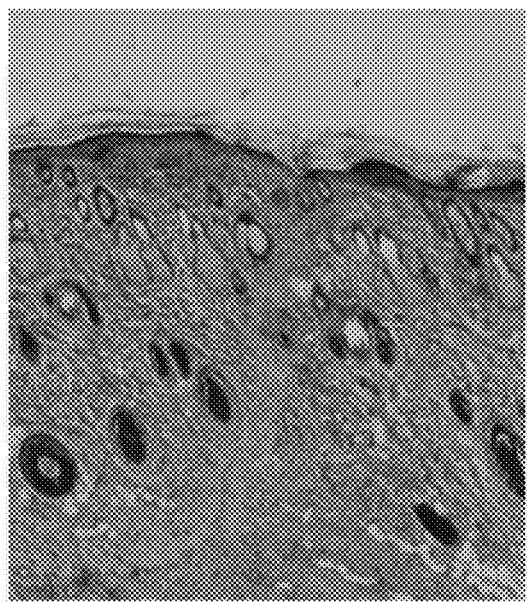
FIG. 5B is a microscopic image of wound tissue that has been treated with a resveratrol ester.

Group 6 demonstrated the most rapid re-epithelialization with 30-50% treatment site re-epithelialization noted at 24 hours compared to 10% in the control sites. The treatment sites showed significantly better re-epithelialization until the $3^{rd}$ postoperative day. Histological comparison revealed a visible decrease in monocytes and fibroblasts in the healing junction. FIG. 5A is a microscopic image of an untreated control incision. FIG. 5B is a microscopic image of an incision treated with a resveratrol ester. The treated incision showed notably uniform epidermal repair as compared to the deep indention of the epidermis seen in the untreated control incision. The differences in fibrosis and mononuclear dermal infiltrates were not considered significant. Moderate to severe trichogranuloma formation was noted in the specimens.

It was postulated that the results may have been different if rat siRNA (MCP-1 inhibitor) had been used instead of human siRNA (MCP-1 inhibitor). It was also suspected that the observed trichogranulomas were caused by rat hair inadvertently entering the incision site during the procedure.

Example 14

In Vivo Application of Various Compositions Containing Resveratrol Esters in a Rat Model (Prophetic)

15 Sprague-Dawley Rats, 6-8 weeks old, will be placed randomly into 5 different groups, Study Groups 1-5, resulting in 3 animals per study group. An incision, 2 cm in length, will be made on both the right and left shoulder of each rat: the left side will be an untreated control, while the right side will be treated with the Compositions 1-5, with the Study Group number corresponding to the Composition number.

Compositions 1-5 will be: (1) 1.25 µg resveratrol trihemiglutarate in 1.0 cc aqueous hydroxypropyl methyl cellulose gel (resveratrol trihemiglutarate concentration=2.19 micromoles/liter); (2) 1.25 µg resveratrol trihemiglutarate in 1.0 cc aqueous high molecular weight hyaluronic acid gel (resveratrol trihemiglutarate concentration=2.19 micromoles/liter); (3) 1.25 µg resveratrol trihemiglutarate and 0.5 g tretinoin in 1.0 cc aqueous hydroxypropyl methyl cellulose gel (resveratrol trihemiglutarate concentration=2.19 micromoles/liter); (4) 1.25 µg resveratrol trihemiglutarate and 0.5 g luteolin in 1.0 cc aqueous hydroxypropyl methyl cellulose gel (resveratrol trihemiglutarate concentration=2.19 micromoles/liter); and (5) resveratrol trihemiglutarate powder.

After each incision is made, the resveratrol trihemiglutarate containing composition will be applied to the right incision just prior to closure using interrupted 5-0 nylon sutures. The left incision will also be closed using interrupted 5-0 nylon sutures. Each incision will be photographed and measurements will be taken, each day for 7 days. On the 4th day, serum blood samples will be taken for systemic absorption assay. On the 7th day, a punch biopsy will be taken from each test and control incision.

Since each skin flap of the incisions will be very close together, when the composition containing resveratrol trihemiglutarate is applied soon after the incision is made, the incision on the right shoulder will heal before fibroplasia begins, so no scar is expected to form. This is in contrast to the otherwise identical incision on the left side, where no resveratrol trihemiglutarate will be applied, which is expected to display a typical scar.

REFERENCES

1. U.S. Pat. Pub. No. US2015/0005391.
2. U.S. Pat. Pub. No. US2011/0245345.
3. U.S. Pat. Pub. No. US2011/0038965.
4. Ehrlich, H. and Krummel, T., "Regulation of wound healing from a connective tissue perspective", Wound Repair & Regeneration, Vol. 4, No. 2, pp. 203-210 (1996).
5. Leung, A. et al., "Fetal wound healing: implications for minimal scar formation", Current Opinion in Pediatrics, Vol. 24, Issue 3, pp. 371-378 (2012).
6. Manuel, J. and Gawronska-Kozak, B., "Matrix metalloproteinase 9 (MMP-9) is upregulated during scarless wound healing in athymic nude mice", Matrix Biology, Vol. 25, pp. 505-514 (2006).
7. Seifert, A. W. et al., "Skin regeneration in adult axolotls: a blueprint for scar-free healing in vertebrates", PLoS One, Vol. 7, Issue 4, e32875 (April 2012).
8. Polette, M. et al., "Tumor invasion and matrix metalloproteinases", Critical Reviews in Oncology/Hematology, Vol. 49, pp. 179-186 (2004).
9. Salo, T. et al., "Expression of matrix metalloproteinase-2 and -9 during early human wound healing", Laboratory Investigation, Vol. 70, Issue 2, pp. 176-182 (February 1994).
10. Giannelis, G., "Matrix metalloproteinases in scarless wound healing", Electronic Theses and Dissertations 2008-2011, July, available online at hdl.handle.net/2429/36241.
11. Guo, M. S. et al., "Hyaluronic acid increases MMP-2 and MMP-9 expressions in cultured trabecular meshwork cells from patients with primary open-angle glaucoma", Molecular Vision, Vol. 18, pp. 11175-11181 (2012).
12. Ndiaye, M. et al., "The grape antioxidant resveratrol for skin disorders: promise, prospects, and challenges", Archive of Biochemistry and Biophysics, Vol. 508, Issue 2, pp. 164-170 (Apr. 15, 2011).
13. Gweon, E. and Kim, S., "Resveratrol induces MMP-9 and cell migration via the p38 kinase and PI-3K pathways in HT1080 human fibrosarcoma cells", Oncology Reports, Vol. 29, Issue 2, pp. 826-834 (February 2013).
14. Ghosh, S. et al., "Resveratrol activates SIRT1 in a Lamin A-dependent manner", Cell Cycle, Vol. 12, Issue 6, pp. 872-876 (Mar. 15, 2013).
15. Blander, G. et al., "SIRT1 promotes differentiation of normal human keratinocytes", Journal of Investigative Dermatology, Vol. 129, Issue 1, pp. 41-49 (January 2009).
16. Thompson, N. L. et al., "Expressions of transforming growth factor-beta 1 in specific cells and tissues of adult and neonatal mice", Journal of Cell Biology, Vol. 108, pp. 661-669 (1989).
17. Midgley, A. et al., "Transforming growth factor-beta 1 (TGF-β1)-stimulated fibroblast to myofibroblast differentiation is mediated by hyaluronan (HA)-facilitated epidermal growth factor receptor (EGFR) and CD44 co-localization in lipid rafts", Journal of Biological Chemistry, Vol. 288, Issue 21, pp. 14824-14838 (May 24, 2013, E-published Apr. 15, 2013).
18. Busch, F. et al., "SIRT-1 is required for the inhibition of apoptosis and inflammatory responses in human tenocytes", Journal of Biological Chemistry, Vol. 287, Issue 31, pp. 25770-25781 (Jul. 27, 2012).
19. Spallotta, F. et al., "A nitric oxide-dependent crosstalk between Class I and II histone deacetylases accelerates skin repair", Journal of Biological Chemistry, Vol. 288, Issue 16, pp. 11004-11012 (Apr. 19, 2013).
20. Pastore, S. et al., "Resveratrol induces long-lasting IL-8 expression and peculiar EGFR activation/distribution in human keratinocytes: mechanisms and implications for skin administration", PLoS One, Vol. 8, Issue 3, e 59632 (2013).
21. Jiang, W. G. et al., "Influence of interleukin-8 (IL-8) and IL-8 receptors on the migration of human keratinocytes, the role of PLC-gamma and potential clinical implications", Experimental and Therapeutic Medicine, Vol. 3, Issue 2, pp. 231-236 (February 2012).
22. Steiger, S. and Harper, J. L., "Neutrophil cannibalism triggers transforming growth factor beta1 production and self regulation of neutrophil inflammatory function in monosodium urate monohydrate crystal-induced inflammation in mice", Arthritis & Rheumatism, Vol. 65, Issue 3, pp. 815-823 (March 2013).
23. Holian, O. and Walter, R. J., "Resveratrol inhibits the proliferation of normal human keratinocytes in vitro", Journal of Cellular Biochemistry Supplement, Vol. 81, Issue S36, pp. 55-62 (2001).
24. Kim, J. J. et al., "The role of SIRT1 on angiogenic and odontogenic potential in human dental pulp cells", Journal of Endodontics, Vol. 38, Issue 7, pp. 899-906 (July 2012).
25. Williams, L. D. et al., "Safety studies conducted on high-purity trans-resveratrol in experimental animals", Food and Chemical Toxicology, Vol. 47, Issue 9, pp. 2170-2182 (September 2009).
26. Polonini, H. C. et al., "Photoprotective activity of resveratrol analogues", Bioorganic & Medicinal Chemistry, Vol. 21, Issue 4, pp. 964-968 (Feb. 15, 2013).
27. Hung, C. F. et al., "Delivery of resveratrol, a red wine polyphenol, from solutions and hydrogels in the skin", Biological and Pharmaceutical Bulletin, Vol. 31, Issue 5, pp. 955-962 (May 2008).
28. Alonso, C. et al., "Antioxidant cosmeto-textiles: skin assessment", European Journal of Pharmaceutics and Biopharmaceutics, Vol. 84, Issue 1, pp. 192-199 (May 2013, E-published Dec. 20, 2012).
29. Machesney, M. et al., "Activated keratinocytes in the epidermis of hypertrophic scars", American Journal of Pathology, Vol. 152, Issue 5, pp. 1133-1141 (May 1998).
30. Fagone, E. et al., "Resveratrol inhibits transforming growth factor-β-induced proliferation and differentiation of ex vivo human lung fibroblasts into myofibroblasts through ERK/Akt inhibition and PTEN restoration", Experimental Lung Research, Vol. 37, Issue 3, pp. 162-174 (April 2011, E-published Jan. 26, 2011).
31. Sheu, S. Y. et al., "Biological characterization of oxidized hyaluronic acid/resveratrol hydrogel for cartilage tissue engineering", Journal of Biomedical Materials Research Part A (Apr. 18, 2013).
32. Fearmonti, R. et al., "A review of scar scales and scar measuring devices", Eplasty (Jun. 21, 2010).
33. Nayor, D. and Kiefer, D., "Living longer, healthier lives with resveratrol", Le Magazine (February 2008).

34. "NEW-SKIN® spray and liquid bandage products", available online at newskinproducts.com/products.aspx (Jun. 20, 2013).

35. "Resveratrol", available online at en.wikipedia.org/wiki/Resveratrol (Jan. 3, 2015).

What is claimed is:

1. A resveratrol ester having the following structure:

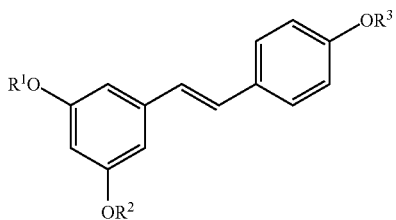

wherein $R^1$, $R^2$ and $R^3$ are

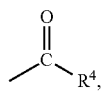

each $R^4$ is independently a carbon chain of 2 to 4 carbon atoms comprising a terminal carboxylic acid moiety, or salts thereof.

2. The resveratrol ester of claim 1, wherein $R^4$ is selected from the group consisting of —$(CH_2)(CO)(OH)$, —$(CH_2)_2(CO)(OH)$, and —$(CH_2)_3(CO)(OH)$.

3. The resveratrol ester of claim 2, wherein $R^4$ is —$(CH_2)_3(CO)(OH)$.

4. The resveratrol ester of claim 1, wherein the ester is selected from the group consisting of resveratrol trihemimalonate, resveratrol trihemsuccinate and resveratrol trihemiglutarate.

5. The resveratrol ester of claim 4, wherein the resveratrol ester is resveratrol trihemiglutarate.

6. A composition, comprising:
the resveratrol ester of claim 1, and
a pharmaceutically acceptable carrier.

7. A composition, comprising:
the resveratrol ester of claim 2, and
a pharmaceutically acceptable carrier.

8. The composition of claim 6, wherein the composition does not include alcohol.

9. A method of making the resveratrol ester of claim 1, comprising:
forming the resveratrol ester from resveratrol.

10. A method of reducing scar formation, comprising:
administering an effective amount of the composition of claim 6, to a patient in need thereof.

11. A method of reducing scar formation, comprising:
administering an effective amount of the composition of claim 7, to a patient in need thereof.

12. A resveratrol ester having the following structure:

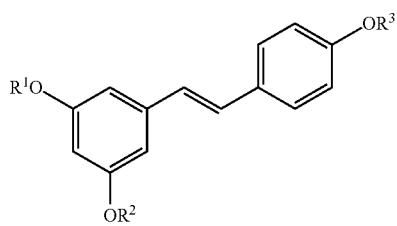

wherein $R^1$, $R^2$ and $R^3$ are H or

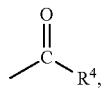

each $R^4$ is

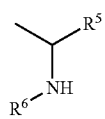

or —$(CH_2)_3(NH)(R^6)$,
at least one $R^1$, $R^2$ and $R^3$ is

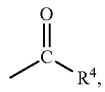

$R^5$ is a natural amino acid side chain, and
$R^6$ is —$(CO)(CH_2)_n(CO)(OH)$ and where n is 1 or 2, or salts thereof.

13. The resveratrol ester of claim 12, wherein $R^6$ is —$(CO)(CH_2)(CO)(OH)$.

14. The resveratrol ester of claim 12, wherein $R^6$ is —$(CO)(CH_2)_2(CO)(OH)$.

15. The resveratrol ester of claim 12, wherein $R^5$ is he natural amino acid side chain of alanine, glycine or valine.

16. A composition, comprising:
the resveratrol ester of claim 12, and
a pharmaceutically acceptable carrier.

17. The composition of claim 16, wherein the composition does not include alcohol.

18. A method of making the resveratrol ester of claim 12, comprising: forming the resveratrol ester from resveratrol.

19. A method of reducing scar formation, comprising:
administering an effective amount of the composition of claim 16, to a patient in need thereof.

* * * * *